(12) United States Patent
Gosselin et al.

(10) Patent No.: US 7,473,708 B2
(45) Date of Patent: Jan. 6, 2009

(54) AGENTS WITH LEUKOTRIENE B$_4$-LIKE ANTIVIRAL (ENVELOPED RNA) ACTIVITIES

(75) Inventors: Jean Gosselin, 935 Émélie-Chamard, Sainte-Foy, Quebec (CA) G1X 4Z9; Pierre Borgeat, Sillery (CA)

(73) Assignee: Jean Gosselin, Quebec (CA)

( * ) Notice: Subject to any disclaimer, the term of this patent is extended or adjusted under 35 U.S.C. 154(b) by 499 days.

(21) Appl. No.: 11/011,016

(22) Filed: Dec. 13, 2004

(65) Prior Publication Data

US 2006/0025479 A1 Feb. 2, 2006

Related U.S. Application Data

(63) Continuation-in-part of application No. 10/683,882, filed on Oct. 10, 2003, now abandoned, which is a continuation-in-part of application No. 09/548,187, filed on Apr. 13, 2000, now abandoned, which is a continuation-in-part of application No. 09/014,553, filed on Jan. 28, 1998, now Pat. No. 6,093,741, which is a continuation-in-part of application No. 08/798,937, filed on Feb. 11, 1997, now Pat. No. 5,789,441, which is a continuation-in-part of application No. 08/602,059, filed on Feb. 15, 1996, now abandoned.

(51) Int. Cl.
*A61K 31/20* (2006.01)
*C07C 69/587* (2006.01)

(52) U.S. Cl. ...................... 514/560; 560/128

(58) Field of Classification Search ............... 514/560; 560/128

See application file for complete search history.

(56) References Cited

U.S. PATENT DOCUMENTS

| 4,689,426 A | 8/1987 | Sugiura et al. ............... 560/121 |
| 6,093,741 A | 7/2000 | Gosselin et al. ............. 514/560 |
| 2002/0028848 A1 | 3/2002 | Buchanan et al. ........... 514/560 |

FOREIGN PATENT DOCUMENTS

| AU | 718069 | 4/2000 |
| EP | 0381823 B1 | 11/1989 |
| WO | WO97/29751 | 8/1997 |
| WO | WO98/24397 | 6/1998 |
| WO | WO02/059072 A2 | 8/2002 |
| WO | WO03/004054 A1 | 1/2003 |

OTHER PUBLICATIONS

Meyer et al. "Enhancement of the action . . . " CA 136:123678 (2002).*
Li et al. "Antithetic . . . " CA 121:279552 (1994).*
Runkel "tTopical drug for the treatment of viral infections" CA 132:9000(1999).*
Lin et al. "Comparative study of . . . " CA 135:313215 (2001).*
Masuda et al. "Effect of anti-herpetic . . . " CA 116:227714 (1992).*
Chemburkar et al. "Dealing with the impact of . . . " CA 133:168261 (2000).*
Fejfarova "Consequences of avian . . . " CAB Accession No. 20063103102 (2005).*
Kelly et al. "Archidonic acid supplementation . . . " Lipids v.33(2) p. 125-130(1998).*
Rola-Pleszczynski et al., *Transplant Proc.*, 18, 44-48 (1986).
Thorson, et al., *AIDS*, 3, 651-653 (1989).
Gewirtz, et al., *J. Clin. Invest.*, 101, 1860-1869 (1998).
Devchand, et al., *Nature*, 384, 39-43 (1996).
Marleau, et al., *Journal of Immunology*, 150, 206-213 (1993).
Marleau, et al., *Br. J. Pharmacol.*, 112, 654-658 (1994).
16th ed. Osol, A., ed., *Remington's Pharmaceutical Sciences*, 1860-1869 (1980).
*Cecil's Text Book of Medicine*, Chapter 164, 19th Edition (1992).
Noverr, M. et al., *Infection and Immunity*, 72; 6206-6210.
Boyum A., Scand. J. Immunol., 1976, 5(5): 9.
Bray, R.A. et al., J. Immunol., 1986, 136: 1783.
Cecil's Textbook of Medicine, chapter 164, 19th Edition, 1992.
Cotran et al., J. Exp. Med., 1986, 164: 661-666.
Devchand P.R. et al., Nature, 1996, 384: 39.
Gagnon L. et al., Cell Immunol. 1987, 110: 243.
Kalmar et al., "Effect of Eicosanoids . . . " CA, 1986, 104: 219747.
Lycke, "Virological aspects on herpesvirus infections" Medline 86151481, 1986.
Marleau et al., Br. J. Pharmacol., 1994, 112: 654.
Marleau et al., J. Immunol., 1993, 150: 206.
Matthews and Boehms, Rev Inf. Dis., 1988, 10,suppl. 3: 490.
Mehl et al., Antimicrob Agents Ch., 1980, 18: 269.
Miller G., Virology, 1990, pp. 1921-1958.
Murphy, The molecular bio. of leukocye chemoattractant receptors, 1994, CA 122:7234.
Nuhn et al., "Synergistic effect of a . . . ", 1987, Derwent Abst. 87-29888.
Papp et al., "Binding of prostacyclin by plasma glycoproteins", 1985, CA104:82673.
Reedman et al., Int. J. Cancer, 1973, 11: 499.
Remington's Pharmaceutical Sciences, 16th ed., 1980.
Rola-Pleszczynski M. et al., Biochem Biophys. Res. Comm., 1982, 108: 1531.

(Continued)

*Primary Examiner*—Celia Chang
(74) *Attorney, Agent, or Firm*—Klauber & Jackson, LLC

(57) ABSTRACT

The present invention relates to the use of the antiviral activity of exogenous leukotriene B$_4$ (LTB$_4$), variants and derivatives thereof as a therapeutic agent in viral infections caused by human and animal enveloped RNA viruses. The human and animal enveloped RNA viruses are RNA viruses, such as togaviridae, orthomyxoviridae, paramyxoviridae, coronaviridae, filoviridae, arenaviridae, bunyaviridae, rhabdoviridae and flaviviridae in general, and Retroviridae such as HIV-1 and HIV-2.

13 Claims, 13 Drawing Sheets

OTHER PUBLICATIONS

Rola-Pleszczynski M. et al., Biochem Biophys. Res. Comm., 1983, 113: 531.

Rola-Pleszczynski M. et al, Prostaglandins Leukotrienes Med., 1984, 13: 113.

Schechter et al., Characterization of a herpes virus . . . Medline 88274329, 1988.

Sinclair et al., "Eicosanoids and the liver", 1990, Medline 92063107.

Steinhart W.L. et al., Virology, 1976, 70: 241.

Toshiki et al. "A patient in whom a PGE1 . . . ", 1995, JICST 02675404.

Bedard M. et al; Poster presented at FASEB Summer Research Conference, Aug. 5-10, 2000.

Abstract of Chen N. et al; (2001) J Neuroimmunol 120(1-2):94-102.

\* cited by examiner

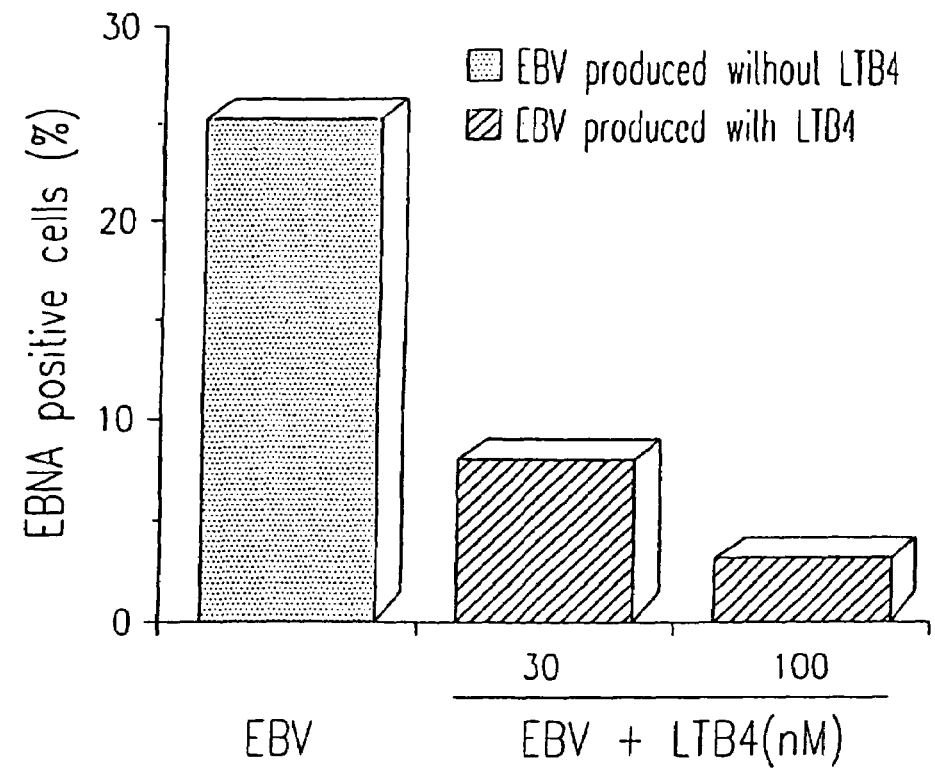
FIG_3
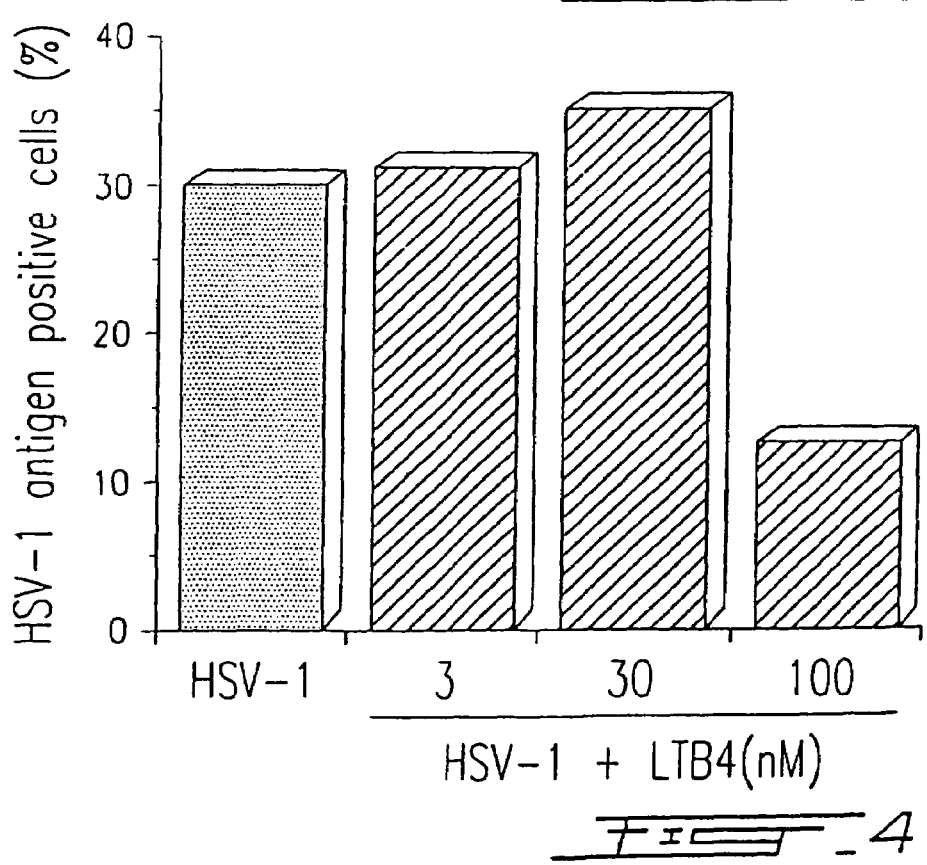
FIG_4

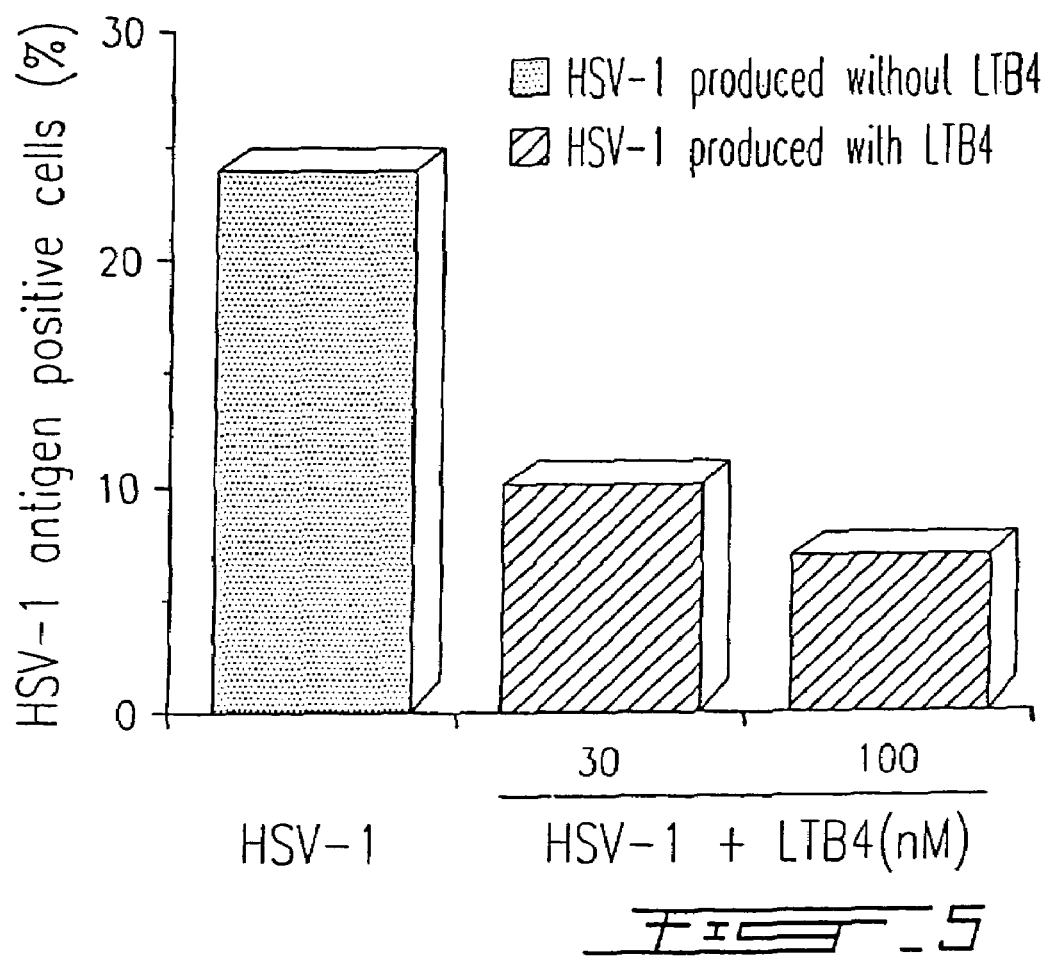

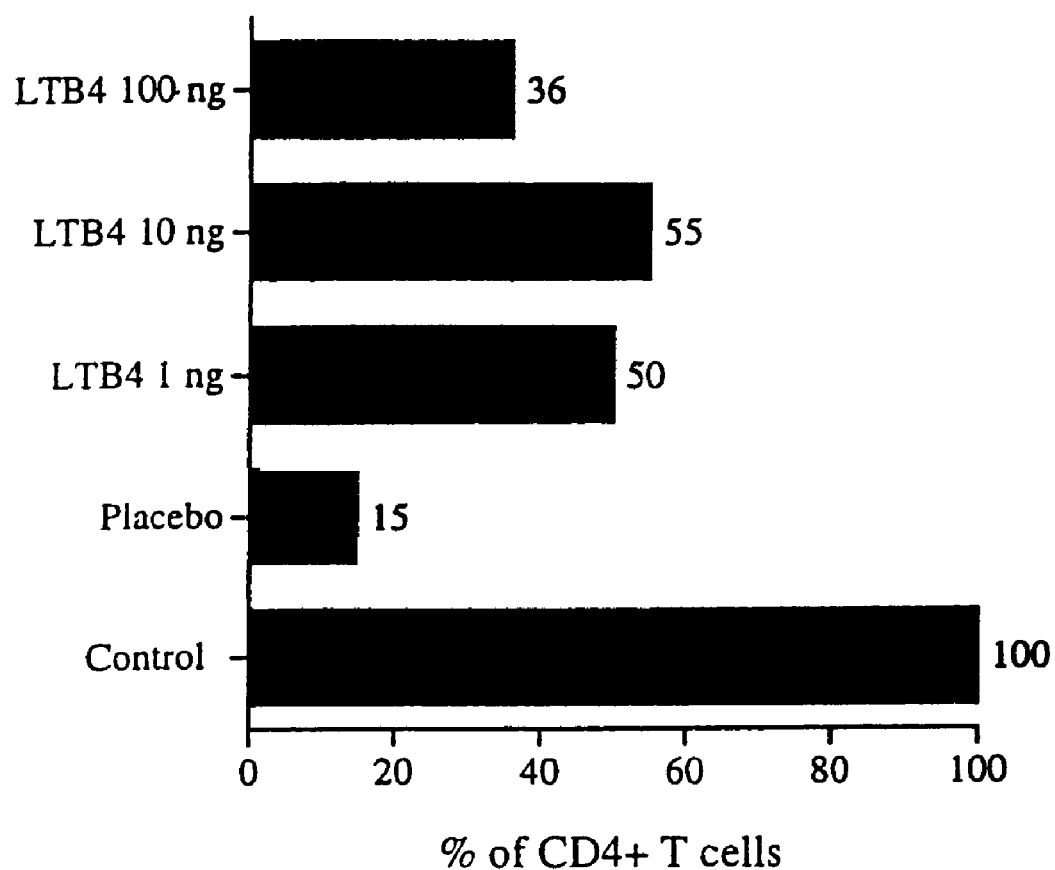
7A

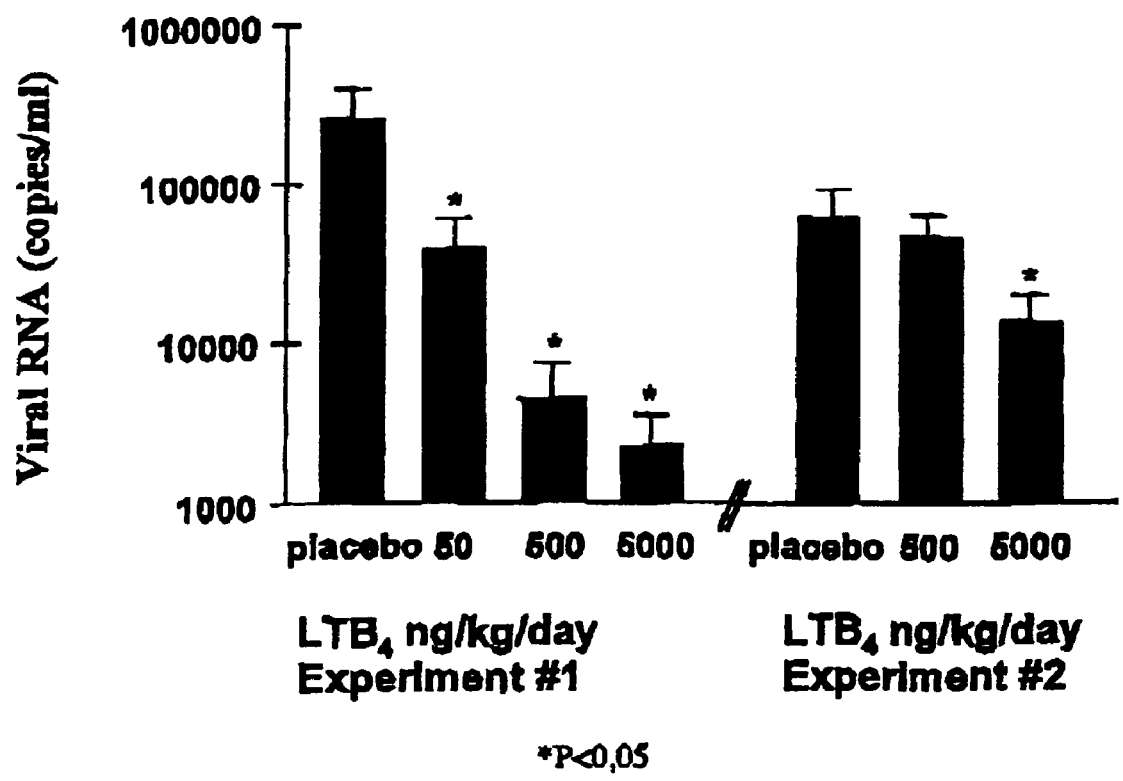

Effects of BG-777 treatment on the viral load of CMV infected mice

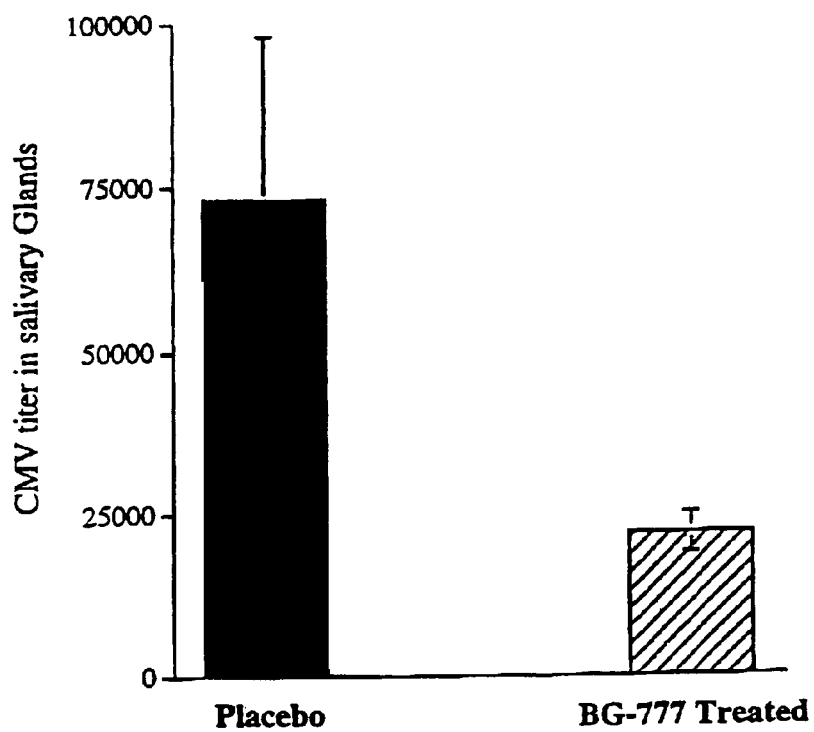

BALB/c mice (5 per group) were infected by intravenous (i.v.) injection with murine CMV. The placebo group received saline while the BG-777 group was administered with 25 ng/mouse of BG-777 (i.v.) once a day for 12 days afterwhich the salivary glands of each mice were harvested and analyzed for CMV viral load.

Results: A 70% reduction (p≤0.008) in the CMV viral load in the salivary glands of BG-777 treated mice was observed compared to the CMV viral load in the salivary glands of placebo treated mice.

Fig. 12B

AGENTS WITH LEUKOTRIENE B₄-LIKE ANTIVIRAL (ENVELOPED RNA) ACTIVITIES

RELATED APPLICATIONS

This is a continuation-in-part of application Ser. No. 10/683,882 filed on Oct. 10, 2003 now abandoned, which is a continuation-in-part of application Ser. No. 09/548,187 filed on Apr. 13, 2000 now abandoned, which is a continuation-in-part of application Ser. No. 09/014,553 filed on Jan. 28, 1998 now U.S. Pat. No. 6,093,741, which is a continuation-in-part of application Ser. No. 08/798,937 filed on Feb. 11, 1997 now U.S. Pat. No. 5,789,441, which is a continuation-in-part of application Ser. No. 08/602,059 filed on Feb. 15, 1996 now abandoned. The entire contents of application Ser. Nos. 10/683,882, 09/548,187, 09/014,553, 08/798,937 and 08/602,059 are hereby incorporated by reference.

BACKGROUND OF THE INVENTION (a) Field of the Invention

The invention relates to the antiviral activity of leukotriene $B_4$ (LTB$_4$), to the use of leukotriene $B_4$ (LTB$_4$) as a therapeutic agent and to a method for treating viral infections caused by human and animal enveloped RNA viruses.

(b) Description of Prior Art

Many important infectious diseases afflicting mankind are caused by viruses. Some are important because they are frequently fatal; among such are rabies, smallpox, poliomyelitis, hepatitis, yellow fever, immune deficiencies and various encephalitic diseases. Others are also important because they are very contagious and create acute discomfort such as influenza, measles, mumps and chickenpox, as well as respiratory-gastrointestinal disorders. Others such as rubella and cytomegalovirus can cause congenital abnormalities. Finally, there are viruses, known as oncoviruses, that can cause tumors and cancer in humans and animals.

Since in the early 1980's, a new disease has been identified and named Acquired Immuno Deficiency Syndrome (AIDS). The human immunodeficiency virus (HIV), which belongs to the Retroviridae family, is known to be the etiologic agent of AIDS. HIV infection in humans can lead to a variety of disease states such as mononucleosis like syndrome, prolonged asymptomatic infection and AIDS. The AIDS' associated diseases include Kaposi's sarcoma, pneumonia, chronic diarrhea, meningitis, toxoplasmosis, encephalopathies, anal-rectal carcinomas and B-lymphocytic lymphomas. The distinctive symptoms of acute infection include lymphadenopathy, fever, myalgia, arthralgia, headache, fatigue, diarrhea, sore throat and neurologic manifestations.

It is now accepted that HIV is transmitted by three main routes: a) sexual contact, b) contaminated blood, and c) from the mother to the fetus. A wide variety of organs and tissues in humans can be invaded by HIV, including bone marrow, lymph node, blood, brain and skin, via the interactions of the viral envelope protein gp120 and the cell surface receptor CD4.

At the end of 1993, an estimated 14 million individuals have been infected with HIV and by the year 2000, this number could be as high as 24 million. Today, medical treatment is limited to the use of antiviral drugs (in particular 3'-azido-3'-deoxythimidine, AZT) and also to the treatment of the many opportunistic infections. However, those treatments are still not fully efficient in the control of HIV infection. Thus, the elaboration of new molecules for the treatment of HIV infection must be given major emphasis.

In all infectious diseases, the efficacy of therapy often depends on the host immune response. This is particularly true for herpes viruses. Indeed, the ability of all herpes viruses to establish latent infections results in an extremely high incidence of reactivated infection in immunocompromised patients. In renal transplant recipients, 40% to 70% reactivate latent HSV infections, and 80% to 100% reactivate CMV infections. Such viral reactivations have also been observed in HIV-positive patients (AIDS).

Today, the number of therapeutic agents used for the treatment of viral infections remain relatively limited. The major compounds used in the treatment of herpes virus infections are idoxuridine, vidarabine, acyclovir and ganciclovir and, more recently famciclovir which is converted in the body into penciclovir. Their efficacy is limited and they cause many side effects. Allergic effects have been reported in 35% of patients treated with idoxuridine which is used only to treat HSV infection of the eye. The most common side effects of vidarabine are gastrointestinal disturbances (15% of patients). The major side effect of acyclovir is the alteration of renal function. Since acyclovir is a nucleoside analog that can be incorporated in both viral and host cell DNA, normal division of host cell can be affected. The most important side effects of gangciclovir are neutropenia and thrombocytopenia that occur in about 40% of AIDS patients.

Thus, there is an urgent need for the development of more efficacious therapeutic agents for the treatment of viral infections with fewer side effects.

Leukotriene B4 (LTB$_4$) [5S,12R-dihydroxy-6,8,10,14 (Z,E,E,Z)-eicosatetraenoic acid] is a known natural molecule. LTB$_4$ is a metabolite of arachidonic acid which is derived from the 5-lipoxygenase pathway. LTB$_4$ has many reported biological properties. In particular, LTB$_4$ is considered as a potent pro-inflammatory compound; its most important biological activity is its chemotactic and chemokinetic effects on leukocytes. Indeed, LTB$_4$ has been shown to be a potent chemoattractant for human polymorphonuclear leukocytes, monocytes and macrophages, both in vitro and in vivo. LTB$_4$ also activates other leukocyte functions such as degranulation and superoxide anion synthesis. Because of these pro-inflammatory effects, LTB$_4$ is considered as a putative component in defense mechanisms. Moreover, LTB$_4$ is synthesized by inflammatory cells such as polymorphonuclear leukocytes, monocytes and macrophages and is also synthetized by B lymphocytes.

LTB$_4$ has also been shown to exert immunomodulatory activities. Indeed, LTB$_4$ was found to induce suppressor cell activity in human peripheral blood mononuclear leukocyte cultures; the induced suppressor cell activity inhibited the proliferative response of human lymphocytes to mitogens (Rola-Pleszczynski M. et al., *BioChem. Biophys. Res. Comm.*, 1982, 108:1531). It was also shown that LTB$_4$ increases human natural cytotoxic cell activity against K562 erythroleukemia cells and against the human prostatic adenoma MA-160 cells either non-infected or persistently infected with Herpes simplex virus type 1 (HSV-1)(Rola-Pleszczynski M. et al., *BioChem. Biophys. Res. Comm.*, 1983, 113:531; Gagnon L., et al., *Cell Immunol.*, 1987, 110:243). Other studies have indicated that in addition to LTB$_4$, LTA$_4$, LTD$_4$, 5-hydroperoxy-eicosatetraenoic acid and 15-hydroperoxy-eicosatetraenoic acid also enhance human natural killer cell cytotoxicity (Rola-Pleszczynski, M. et al, *Prostaglandins Leukotrienes Med.*, 1984, 13:113; Bray, R. A. et al. *J. Immunol*, 1986, 136:1783).

A family of molecules collectively called the prostaglandins (prostaglandins A, B, D, J, E and I) which are structurally related to LTB$_4$, have been repeatedly demonstrated to exert antiviral and anti-cancer activity both in in vitro and in vivo systems. The prostaglandins are derived from arachidonic acid, as for $LTB_4$, but originate from a different biosynthetic pathway, the cyclooxygenase pathway.

U.S. Pat. No. 4,689,426 issued on Aug. 25, 1987 in the name of Sugiura et al. describes cyclopentenone derivatives related to prostaglandin A or D which possess anti-tumor and antiviral activities.

Although, some prostaglandins have been shown to have antiviral activities, they caused undesirable side effects, and exhibited relatively low activity.

It would be highly desirable to be provided with an antiviral agent with greater efficacy for enveloped RNA viruses and which would not present the undesirable side effects of the known antiviral agents.

SUMMARY OF THE INVENTION

One aim of the present invention is to provide an antiviral agent and method which would be effective for the prophylaxis and the treatment of viral infections (enveloped RNA viruses) and would not present the undesirable side effects of the known antiviral agents.

Another aim of the present invention is to provide an antiviral agent for the prophylaxis or treatment of viral infections in immunosuppressed patients and animals.

In accordance with one aspect of the invention there is provided a method for the prophylaxis or treatment of a viral infection in a human or animal comprising administering to a human or animal in need of such treatment, a pharmacologically acceptable therapeutically effective amount of $LTB_4$ agent.

In accordance with another aspect of the invention there is provided an antiviral pharmaceutical formulation comprising a pharmacologically acceptable, therapeutically effective amount of a $LTB_4$ agent and a pharmaceutically acceptable carrier.

In accordance with the present invention there is provided the use of a $LTB_4$ agent as an antiviral agent against HIV-1 and HIV-2 and against other human and animal enveloped RNA viruses, including, but not limited to, influenza virus belonging to the orthomyxoviridae, hepatitis C virus belonging to the flaviviridae ans SARS-coronavirus belonging to the coronaviridae.

In accordance with the present invention there is provided the use of a $LTB_4$ agent as an antiviral agent in the treatment of viral infections in humans and animals in association with other antiviral agents, including but not limited to interferon-$\alpha$, -$\beta$, -$\gamma$, tumor necrosis factor $\alpha$, ganciclovir, acyclovir, vidarabine, idoxuridine, famciclovir 3TC, crixivan, nevarepine and prostaglandins or prostaglandin analogs.

In accordance with the present invention, there is provided the use of a $LTB_4$ agent as an antiviral agent for the prophylaxis and treatment of viral infections in immunosuppressed patients and animals.

Immunosuppressed patients include patients who underwent organ or tissue transplantation and are treated with immunosuppressive agents including but not limited to azathioprine, corticosteroids, adriamycine, cyclophosphamide and methotrexate. Immunosuppressed patients also include patients with any form of cancer or neoplasic diseases treated or not with anti-neoplastic chemotherapeutic agents including but not limited to adriamycine, cyclophosphamide and methotrexate. Immunosuppressed patients also include patients with inflammatory diseases treated with anti-inflammatory agents including but not limited to corticosteroids, methotrexate, azathioprine and cyclophosphamide. Immunosuppressed patients also include patients with shock or severe trauma including but not limited to burn injury, or patients undergoing chronic hemodialysis.

In accordance with the present invention, there is provided the use of a $LTB_4$ agent as an antiviral agent against viral infections in immunosuppressed patients and animals in association with other antiviral agents.

In accordance with the present invention, there is also provided the use of a $LTB_4$ agent as an antiviral agent for the prophylaxis and treatment of viral infections in humans and animals in association with other agents including but not limited to granulocyte-macrophage colony-stimulating factor (GM-CSF), granulocyte colony stimulating factor (G-CSF), macrophage colony stimulating factor (M-CSF), interferons, tumor necrosis factor $\alpha$, interleukin-3 and interleukin-5, which have been shown to prime leukocytes for the synthesis of $LTB_4$ or other arachidonic acid metabolites (including several $LTB_4$ agents) and may potentiate the antiviral activity of the $LTB_4$ agent.

In accordance with the present invention, there is provided the use of a $LTB_4$ agent as an antiviral agent in the prophylaxis or treatment of viral infections in humans and animals in association with retinoids including but not limited to 9-cis-retinoic acid and analogs (such as 13-cis-retinoic acid or all trans-retinoic acid), which are ligands of retinoid receptors, and may potentiate the antiviral activity of the $LTB_4$ agent.

In accordance with the present invention, there is provided the use of a $LTB_4$ agent as an antiviral agent for the prophylaxis and treatment of viral infections in animals and humans in association with nonsteroidal anti-inflammatory drugs including but not limited to N-acetyl salicylic acid, indomethacin, ibuprofen, flurbiprofen and naproxen, which are inhibitors of the type I (constitutive) and II (inducible) cyclo-oxygenases, and might be useful in limiting potential side effects of the administration of $LTB_4$ agents in humans and animals.

BRIEF DESCRIPTION OF THE DRAWINGS

FIG. 3 illustrates the effects of $LTB_4$ on the production of EBV particles;

FIG. 4 illustrates the effects of $LTB_4$ on HSV-1-induced synthesis of cytoplasmic antigens;

FIG. 5 illustrates the effects of $LTB_4$ on the production of HSV-1 particles;

FIG. 7A illustrates the effects of $LTB_4$ on CD4+ T cell survival;

FIG. 7B illustrates HIV viral load in HIV-infected mice;

FIG. 12B illustrates the effect of $LTB_4$ on viral load of CMV-infected mice in salivary glands.

DETAILED DESCRIPTION OF THE INVENTION i) $LTB_4$

Figure 1:
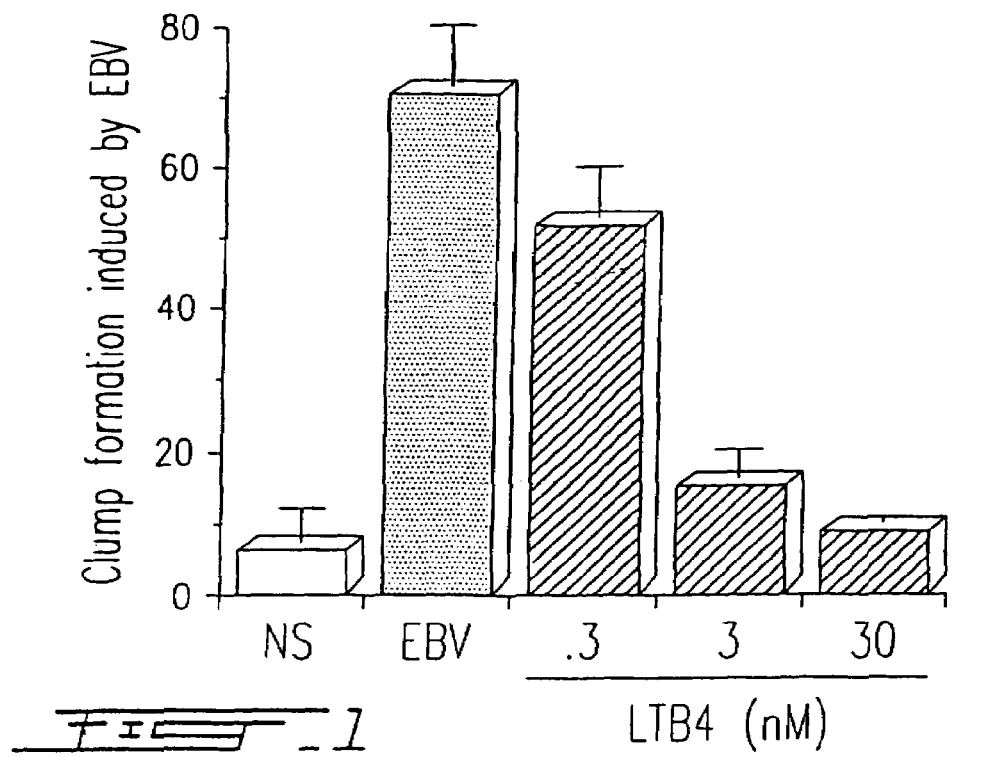
FIG. 1 illustrates the effects of $LTB_4$ on clump formation induced by EBV.

The leukotriene B4 ($LTB_4$) agent of the present invention is either $LTB_4$ or certain structurally related polyunsaturated fatty acids, or substances structurally unrelated to fatty acids, which stimulate the synthesis of $LTB_4$ or other $LTB_4$ agents by cells, or mimic their biological activity. They are either natural substances or analogs of such natural substances. All of the $LTB_4$ agents can be obtained by chemical synthesis by methods described in the literature and most are commercially available.

As used herein, the term "$LTB_4$ agent" means one or more of the following polyunsaturated fatty acids, which in addition to $LTB_4$ itself, are analogs of $LTB_4$, or precursors or metabolites of $LTB_4$ or $LTB_4$ analogs: $LTB_4$, 14,15-dihydro-$LTB_4$, 17,18-dehydro-$LTB_4$, 19-hydroxy-$LTB_4$, 20-hydroxy-$LTB_4$ and their 5(R)-hydroxy, 5-keto, 5(S)hydroperoxy, 5(R)-hydroperoxy and 5-deoxy analogs; $LTA_4$; 14,15-dihydro-$LTA_4$, 17,18-dehydro-$LTA_4$; 5(S)-hydroxy-6,8,11,14(E,Z,Z,Z)-eicosatetraenoic acid ("5-HETE"), 14,15-dihydro-5-HETE, 17,18-dehydro-5-HETE, and their 5(R)-hydroxy, 5-keto, 5(S)-hydroperoxy, 5(R)-hydroperoxy analogs; 12(R)-hydroxy-5,8,10,14(Z,Z,E,Z)-eicosatetraenoic acid ("12-HETE"), 5,6-dihydro-12-HETE, 14,15-dihydro-12-HETE, 17,18-dehydro-12-HETE and their 12(S)-hydroxy, 12-keto, 12(S)-hydroperoxy and 12(R)-hydroperoxy analogs and 12-oxo-5,8,10(Z,Z,E)-dodecatrienoic acid, 15(S)-hydroxy-5,8,11,13(Z,Z,Z,E)-eicosatetraenoic acid ("15-HETE"), 5,6- dihydro-15-HETE, 17,18-dehydro-15-HETE and their 15(R)-hydroxy, 15-keto, 15(S)-hydroperoxy, and 15(R)-hydroperoxy analogs.

The term $LTB_4$ agent also includes other derivatives of polyunsaturated fatty acids; some are derived from the cyclooxygenase pathways, the lipoxygenase pathways (5-, 12- and 15-lipoxygenases) or the cytochrome P450 pathways; others are isomers, analogs or derivatives of naturally formed compounds: 12(S)-hydroxy-5,8,10(Z,E,E)-heptadecatrienoic acid; leukotrienes $C_4$, $D_4$ and $E_4$ and their 14,15-dihydro or 17,18-dehydro analogs; N-acyl or N-alkyl derivatives of leukotrienes $C_4$, $D_4$ and $E_4$, and their 14,15-dihydro or 17,18-dehydro analogs; all isomeric 5,12-dihydroxy-6,8,10,14-eicosatetraenoic acids and their 14,15-dihydro or 17,18-dehydro analogs; all isomeric 5,6-dihydroxy-7,9,11,14-eicosatetraenoic acids and their 14,15-dihydro or 17,18-dehydro analogs; all isomeric 5,15-dihydroxy-6,8,11,13-eicosatetraenoic acids (including 5(S),15(S)-dihydroxy-6,8,11,13(E,Z,Z,E)-eicosatetraenoic acid) and their 17,18-dehydro analogs; all isomeric 8-hydroxy-11(12)-epoxy-5,9,14-eicosatrienoic acids (including hepoxilin A3) and their 5,6-dihydro or 14,15-dihydro or 17,18-dehydro analogs; all isomeric 10-hydroxy-11(12)-epoxy-5,8,14-eicosatrienoic acids (including hepoxilin B3) and their 5,6-dihydro or 14,15-dihydro or 17,18-dehydro analogs; all isomeric 8,11,12-trihydroxy-5,9,14-eicosatrienoic acids (including trioxilin $A_3$) and their 5,6-dihydro or 14,15-dihydro or 17,18-dehydro analogs; all isomeric 10,11,12-trihydroxy-5,8,14-eicosatrienoic acids (including trioxilin B3) and their 5,6-dihydro or 14,15-dihydro or 17,18-dehydro analogs; all isomeric 11(12)-epoxy-5,7,9,14-eicosatetraenoic acid and their 14,15-dihydro or 17,18-dehydro analogs; all isomeric 11,12-dihydroxy-5,7,9,14-eicosatetraenoic acids and their 14,15-dihydro or 17,18-dehydro analogs; all isomeric 8(9)-epoxy-5,10,12,14-eicosatetraenoic acids and their 5,6-dihydro or 17,18-dehydro analogs; all isomeric 8,9-dihydroxy-5,10,12,14-eicosatetraenoic acids and their 5,6-dihydro or 17,18-dehydro analogs; all isomeric 8,15-dihydroxy-5,9,11,13-eicosatetraenoic acids and their 5,6-dihydro or 17,18-dehydro analogs; all isomeric 14(15)-epoxy-5,8,10,12-eicosatetraenoic acids and their 5,6-dihydro or 17,18-dehydro analogs; all isomeric 14,15-dihydroxy-5,8,10,12-eicosatetraenoic acids and their 5,6-dihydro or 17,18-dehydro analogs; all isomeric 5-hydroxy-14(15)-epoxy-6,8,10,12-eicosatetraenoic acids and their 17,18-dehydro analogs; all isomeric 5,14,15-trihydroxy-6,8,10,12-eicosatetraenoic acids (including lipoxin $B_4$) and their 17,18-dehydro analogs; all isomeric 5,6,15-trihydroxy-7,9,11,13-eicosatetraenoic acids (including lipoxin $A_4$) and their 17,18-dehydro analogs; all isomeric 5(6)-epoxy-15-hydroxy-7,9,11,13-eicosatetraenoic acids and their 17,18-dehydro analogs; all isomeric 5-hydroxy-6,8,11,14-eicosatetraenoic acids and their 14,15-dihydro or 17,18-dehydro analogs; all isomeric 8-hydroxy-5,9,11,14-eicosatetraenoic acids and their 5,6-dihydro or 14,15-dihydro or 17,18-dehydro analogs; all isomeric 9-hydroxy-5,7,11,14-eicosatetraenoic acids and their 14,15-dihydro or 17,18-dehydro analogs; all isomeric 11-hydroxy-5,8,12,14-eicosatetraenoic acids and their 5,6-dihydro or 17,18-dehydro analogs; all isomeric 12-hydroxy-5,8,10,14-eicosatetraenoic acids and their 5,6-dihydro or 14,15-dihydro or 17,18-dehydro analogs; all isomeric 15-hydroxy-5,8,11,13-eicosatetraenoic acid and their 5,6-dihydro or 17,18-dehydro analogs; all isomeric 9-hydroxy-10,12-octadecadienoic acids; all isomeric 13-hydroxy-9,11-octadecadienoic acids; 12(R)-hydroxy-5,8,14(Z,Z,Z)-eicosatrienoic acid; all isomeric 5(6)oxido- or 5,6-dihydroxy-8,11,14-eicosatrienoic acids and their 14,15-dihydro or 17,18-dehydro analogs; all isomeric 8(9)-oxido- or 8,9-dihydroxy-5,11,14-eicosatrienoic acids and their 5,6-dihydro or 14,15-dihydro or 17,18-dehydro analogs; all isomeric 11(12)-oxido- or 11,12-dihydroxy-5,8,14-eicosatrienoic acids and their 5,6-dihydro or 14,15-dihydro or 17,18-dehydro analogs; all isomeric 14(15)-oxido- or 14,15-dihydroxy-5,8,11-eicosatrienoic acids and their 5,6-dihydro or 17,18-dehydro analogs.

The term $LTB_4$ also includes variants which are non-covalently modified fatty acids such as the sodium or the potassium salts of the $LTB_4$ agents.

The term $LTB_4$ agent also includes variants where a modification is introduced into the molecule by reacting targeted functional groups of the fatty acid with an organic derivatizing agent that is capable of reacting with the selected functional group (yielding for example, ester and ether derivatives of $LTB_4$ agent) or to cause intramolecular rearrangement (such as the formation of lactones with hydroxylated fatty acids). The resulting compounds may have altered biological activity and/or bioavailability. Thus, the covalently modified fatty acid can be a pro-drug with reduced biological activity which upon in vivo administration is slowly transformed into a more active molecule (underivatized $LTB_4$ agent). Variants may also be metabolically stable and biologically active analogs of $LTB_4$ agents altered in a way that will result in retarded disposition of the compound (decreased metabolism and/or elimination). Variants with modifications at the omega end (such as 20,20,20-trifluoromethyl-$LTB_4$) show increased resistance to omega-oxidation (a catabolic process of unsaturated fatty acids); other variants with modification at the omega end at the level of carbons 13 to 20 (such as 19-methyl-$LTB_4$ or 19,19-dimethyl-$LTB_4$ or 19-fluoro-$LTB_4$ or 19,19-difluoro-$LTB_4$ or 18,20-difluoro-$LTB_4$ or 20-fluoro-$LTB_4$) may show increased resistance to omega-oxidation and variants with modifications at the carboxylic end, at the level of carbon 1, 2, 3 or 4 (for example, 3-thio-$LTB_4$, 3-hydroxy-$LTB_4$, 3-methyl-$LTB_4$ or 3,3-dimethyl-$LTB_4$ or 3-fluoro-$LTB_4$ or 3,3-difluoro-$LTB_4$ or 2,3-difluoro-$LTB_4$, $LTB_4$ methylsulfonylamide, $LTB_4$ methylamide, 1-tetrazole $LTB_4$), may show increased metabolic resistance to beta-oxidation and/or to elimination (such as uptake by probenecide-sensitive organic acid transporter). Other variants with modification(s) at carbon 12, such as 12(R)-methyl-$LTB_4$, may show increased resistance to reduction of the 11,12 double bond (a metabolic pathway of $LTB_4$). Other variants are analogs of $LTB_4$ agents with structural changes, such as changes in chain length (chain length increased or decreased by up to 4 carbons), addition of double bond(s), saturation of double bond(s), changes in double bond(s) geometry (cis to trans or vice versa), change of double bond(s) for triple bond(s), change in the configuration of one or several functional group(s) (R to S or S to R), or where one or several functional group(s) or substituent(s) are either removed, added or changed for other functional groups or substituents (including but not limited to hydroperoxyl, carbonyl, sulfhydryl, sulfoxide, sulfone, cysteinyl, glutathionyl, cysteinyl-glycine, methyl, isopropyl, benzyl, chloro, fluoro), or where the positions of one or several functional groups and/or one or several double bonds has been moved by one, two or three carbons relative to the omega end. The $LTB_4$ agent may be a variant carrying one or several of the above mentioned structural modifications.

The $LTB_4$ agents and variants of $LTB_4$ agents are structurally related to $LTB_4$ and bind or may bind with different affinities to either the cell surface binding sites of $LTB_4$ (or other related eicosanoids, including but not limited to 5-HETE, $LTD_4$, lipoxin $A_4$) present on various leukocytes (and other cell types), or to the nuclear binding site of $LTB_4$, the transcription factor PPARα (peroxisome proliferator-activated receptor alpha) (Devchand P. R., et al., *Nature* 384:39, 1996), or to other unknown binding sites of $LTB_4$, resulting in the expression of the biological activities of $LTB_4$ and $LTB_4$ agents. The $LTB_4$ agents and variants show or may show biological activities qualitatively similar to that of $LTB_4$ (but may be more or less active than $LTB_4$ itself) and thus can be expected to exert an antiviral activity similar to that of $LTB_4$. The $LTB_4$ agents and variants thereof are included within the scope of this invention.

The term $LTB_4$ agent also includes agents not structurally related to $LTB_4$ including but not limited to the chemotactic peptide formyl-met-leu-phe (fMLP) (and analogs such as N-formyl-nle-leu-phe, N-formyl-met-leu-phe-benzylamide, N-formyl-met-leu-phe-methyl-ester and N-formyl-Nle-leu-phe-nle-tyr-lys), the complement fragment C5a and analogs, and the biologically active phospholipid platelet-activating factor, 1-0-hexadecyl-2-0-acetyl-sn-glycero-3-phosphocholine (and analogs such as 1-0-octadecyl-2-0-sn-glycero-3-phosphocholine and 1-0-hexadecyl-2-N-methyl-carbamyl-sn-glycero-3-phosphocholine) that stimulate or may stimulate the release of unsaturated fatty acids in cells (mainly arachidonic acid) and consequently the formation of one or several $LTB_4$ agents, and may therefore exhibit an antiviral activity similar to that of $LTB_4$. The above-mentioned $LTB_4$ agents not structurally related to $LTB_4$ are thus included within the scope of this invention.

The term $LTB_4$ agent also includes formulations of compounds which might contain a mixture of two or several $LTB_4$ agents or an $LTB_4$ agent and one or several equally or less active isomer(s) of the $LTB_4$ agent (positional, geometrical or optical isomers).

ii) Viral Infections

The viral infections which may be treated with the $LTB_4$ agent, in accordance with the invention, are infections caused by human and/or animal viruses.

The expression "human and/or animal viruses" is intended to include, without limitation, enveloped RNA viruses in general. Enveloped RNA viruses include togaviridae, orthomyxoviridae, paramyxoviridae, coronaviridae, filoviridae, arenaviridae, bunyaviridae, rhabdoviridae, flaviviridae and Retroviridae.

The antiviral activity of $LTB_4$ against three herpes viruses, EBV, CMV and HSV-1 and against 3 enveloped RNA virus (HIV, Influenza and coronavirus) have been studied. Human peripheral blood mononuclear cells were cultured in the presence or absence of $LTB_4$ at different concentrations. After ten to twelve days of culture, two parameters were evaluated: the formation of clumps or rosettes, which morphologically characterizes the EBV-infected cells, and the presence of Epstein-Barr Nuclear Antigen (EBNA), a viral antigen synthesized in EBV-infected cells. The results obtained show that $LTB_4$ markedly affected the formation of clumps. Similarly, the percentage of EBNA-positive cells was strongly decreased by more than 56% with 30 nM $LTB_4$ and by more than 70% with a concentration of 100 nM. Similar results were also obtained with HVS-1 and HIV-1. In fact, the presence of $LTB_4$ (100 nM) in the cellular cultures strongly inhibited the synthesis of specific HSV-1 antigen by more than 60%, and suppressed the reverse transcriptase activity by more than 70% in HIV-1 infected PBMC. Interestingly, in all cellular cultures, the cell viability was comparable to that of the unstimulated cells (controls) cultured during the same period of time, indicating that $LTB_4$ exerts no direct cytotoxic effect on the cells. Furthermore, $LTB_4$ was found to inhibit (>80%) the formation of new EBV particles produced in B95-8 cells. This effect was also observed with HSV-1 (75% inhibition) and HIV-1 (>55% inhibition) using Vero cells and J1.1 cells, respectively. In an in vivo experimental model (hairless mice), skin lesions generated by HSV-1 inoculation were smaller and disappeared more rapidly in animals treated with $LTB_4$ (10 g intraperitoneally). Beneficial effects of $LTB_4$ were also observed in mice infected with CMV, coronavirus or Influenza virus. In fact, compared to the placebo-treated group, mice that received $LTB_4$ had reduced CMV, coronavirus and Influenza viral loads. These results clearly show that the $LTB_4$ exerts a very potent antiviral effect against three herpes viruses and 3 enveloped RNA viruses.

Some $LTB_4$ agents (other than $LTB_4$ itself) were tested and found to exert an antiviral effect on HSV-1 or EBV in vitro. When added to cell culture media (four consecutive additions of 100 pmol/ml throughout the 7-10 days incubation period), the $LTB_4$ agents 20-hydroxy-$LTB_4$, 12(R)-HETE, 14,15-dihydro-$LTA_4$ methyl ester, and N-formyl-met-leu-phe, inhibited the infection of peripheral blood mononuclear leukocytes by HSV-1 (as assessed by the presence of HSV-1 antigens) or the production of HSV-1 particles in Vero cells, by 40% or more. In the same experiments, the antiviral agent acyclovir used at a 10 times greater concentration had similar effects. The $LTB_4$ agents 5(S),15(S)-dihydroxy-6,8,11,13-(E,Z,Z,E)-eicosatetrae-noic acid (5,15-diHETE), 14,15-dihydro-$LTA_4$ methyl ester, $LTB_4$ methyl ester and N-formyl-met-leu-phe, inhibited the infection of peripheral blood mononuclear leukocytes by EBV (as assessed by the presence of the EBV antigen EBNA) or the production of EBV particles in B95-8 cells by 40% or more. While the mechanism(s) of the antiviral effect of $LTB_4$ agents is unknown, the antiviral activity observed for some $LTB_4$ agents, in particular the 5,15-diHETE, which is a weak agonist of the cell membrane receptors of LTB$_4$, suggests that the site of action of the LTB$_4$ agents may not be the cell surface receptors of LTB$_4$, but rather the intracellular (nuclear) binding site of LTB$_4$, the transcription factor peroxisome proliferator-activated receptor (PPARα). Indeed, PPARα is known to be responsive to a wide variety of lipophilic molecules, including unsaturated fatty acids, hypolipidemic drugs (fibrates), glucocorticoids, the prostacyclin (PGI$_2$) stable analog Iloprost and xenobiotics, which indicates a relatively low selectivity of the PPARα binding site-ligand interaction. It thus seems likely that a lipophilic compound such as 5,15-diHETE, which is a close structural analog of LTB$_4$ (both compounds are dihydroxylated derivatives of arachidonic acid) could also be a ligand of PPARα. In fact, it is likely that a wide range of unsaturated fatty acids structurally related to LTB$_4$ could bind to PPARα. PPARs constitute a family of transcription factors that control the expression of a number of enzymes involved in lipid metabolism (including fatty acid degradation) and thus control lipid homeostasis. Because viral replication implies the formation of lipid-containing structures (capsid, envelope), activation of PPARα by LTB$_4$ agents may exert antiviral effects by interfering in viral assembly processes. It is interesting that Steinhart W. L., et al (*Virology* 70:241, 1976) and Mehl J. K., et al. (*Antimicrob. Agents Ch.* 18: 269, 1980) have previously reported an antiviral activity of clofibrate and procetophene (two hypolipidemic drugs known to activate PPARα) on HSV-1 in vitro. However, it remains distinctly possible that the binding to and activation of PPARα by LTB$_4$ agents may trigger yet unknown cellular events, resulting in an antiviral activity; furthermore, it is not excluded that LTB$_4$ agents could bind and activate other transcription factor(s).

It is noteworthy that ganciclovir was shown to have IC$_{50}$ values of 1 and 2.4 μM in in vitro assays of viral replication (EBV and HSV, respectively)(Matthews and Boehms, *Rev Inf. Dis.*, 1988, 10, suppl. 3:490). Preliminary comparative studies show that, in vitro LTB$_4$ exerts potent antiviral activity as compared to acyclovir. It is possible that the structure of LTB$_4$ could be modified in order to provide a molecule with even higher antiviral activity or alternatively, a molecule with increased bioavailability (for example, decreased lipophilicity or enhanced resistance to metabolism in vivo).

Thus, the results indicate that LTB$_4$ is useful in the treatment of viral infections in humans and animals. Because these data show that LTB$_4$ exerts antiviral activity against six types of viruses, and thus is not specific to a single type of virus, it is expected to be useful for the treatment of viral infections caused by any type of viruses.

Prostaglandins (A, B, D, J, E and I) are found to be less active, on a molar basis, than LTB$_4$ when tested in vitro.

iii) Dose Ranges

The therapeutically effective amount of the LTB$_4$ agent to be administered will vary with the particular LTB$_4$ agent used, the type or mode of administration, the concurrent use of other active compounds, host age and size, type, severity and spread of infection, response of individual patients, and the like. In the case of LTB$_4$, it will be administered in sufficient doses to obtain an effective peak or steady-state concentration of about 0.25 nM to 1000 nM, preferably of about 0.25 nM to 25 nM, and more preferably of about 0.25 nM to about 2.5 nM. An effective dose amount of the LTB$_4$ agent is thus be determined by the clinician after a consideration of all the above-mentioned criteria. In the case of LTB$_4$ agents other than LTB$_4$ which have a different biological activity, the effective peak or steady-state concentration required may be different, for instance up to 10 μM. The dosage amount of agent necessary to obtain the desired concentrations in blood can be determined by pharmacokinetic studies, as described in Marleau et al., *J. Immunol.* 150: 206, 1993, and Marleau et al, *Br. J. Pharmacol.* 112: 654, 1994.

iv) Pharmaceutical Compositions

Any suitable type or mode of administration may be employed for providing a mammal, especially a human with an effective dosage of a LTB$_4$ agent of the present invention. For example, oral, parenteral and topical may be employed. Dosage forms include tablets, capsules, powders, solutions, dispersions, suspensions, creams, ointments and aerosols.

The pharmaceutical compositions of the present invention comprise a LTB$_4$ agent as an active ingredient, and a pharmaceutically acceptable carrier and optionally other therapeutic ingredients.

It should be recognized that the LTB$_4$ agent can be used in a variety of ways in vivo. It can be formulated into pharmaceutical compositions according to any known methods of preparing pharmaceutically useful compositions. In this manner, the fatty acid is combined in admixture with a pharmaceutically acceptable carrier vehicle. Suitable vehicles and their formulation, including human proteins, e.g., human serum albumin, are described for instance in *Remington's Pharmaceutical Sciences* (16th ed. Osol, A., ed., Mack, Easton, Pa. [1980]). In order to form a pharmaceutically acceptable composition suitable for effective administration, such compositions will contain a therapeutically effective amount of the LTB$_4$ agent or amount resulting in antiviral activity, together with a suitable amount of carrier vehicle. The amounts required for antiviral effects can be determined by in vivo pharmacological studies.

The LTB$_4$ agent can be formulated as a sterile pharmaceutical composition for therapeutic use which is suitable for intravenous or intraarterial administration. The product may be in a solvent-free form and ready to be reconstituted for use by the addition of a suitable carrier or diluent, or alternatively, it may be in the form of solution which may be aqueous or organic.

For reconstitution of a solvent-free product in accordance with the present invention, one may employ a sterile diluent, which may contain materials generally recognized for approximating physiological conditions. In this manner, the sterile diluent may contain salts and/or buffering agents to achieve a physiologically acceptable tonicity and pH, such as sodium chloride, phosphate and/or other substances which are physiologically acceptable and/or safe for use.

When used as an aqueous solution, the pharmaceutical composition will for the most part contain many of the same substances described above for the reconstitution of a solvent-free product. When used in solution in an organic solvent, a small volume of the solution containing the fatty acid will be diluted with an aqueous solution that will contain many of the same substances described above for the reconstitution of a solvent-free product. The pharmaceutical composition, for the most part, will thus contain many of the same substances described above for the reconstitution of a solvent-free product.

The LTB$_4$ agent useful in the methods of the present invention may be employed in such forms as, for example, sterile solutions for injection or encapsulated (for instance in liposomes) or embedded (for example in suppositories) for slower long-lasting release.

The LTB$_4$ agent may be used in combination with other agents including, but not limited to, anti-viral agents, anti-cancer agents, immunosuppressive agents, anti-inflammatory agents, cytokines, retinoids and compounds that may reduce uptake, elimination or metabolism of the $LTB_4$ agent such as probenecide, dipyridamole or clofibrate.

Where the subject $LTB_4$ agent is to be administered to a host as an anti-viral agent, the agent may be administered, for example, intraarterially, intravenously, intraperitoneally, subcutaneously, intramuscularly, by injection, by inhalation, by suppository, or the like. Because of the high cost of most $LTB_4$ agents and their chemical stability, injection of $LTB_4$ may represent the most advantageous form of administration of the composition of the present invention to a patient in order to achieve a better control of the dosage. The mode of administration by injection includes continuous infusion as well as single or multiple boluses. Given the short half-life of some $LTB_4$ agents in the circulation (Marleau et al., Br. J. Pharmacol. 112: 654, 1994), their administration as single or multiple boluses may imply the simultaneous use of agents to retard elimination of $LTB_4$ agent and/or to inhibit its metabolism, or alternatively, the use of analogs of $LTB_4$ agents with prolonged half-life in the circulation. Useful administration type or mode also includes the use of implantable internal pumps for continuous infusion into a blood vessel or at different sites such as the peritoneal cavity or subcutaneously. Such techniques are disclosed in Cecil's Text Book of Medicine (Chapter 164, 19th Edition, 1992) for the treatment of hepatic cancers. Transdermal administration by means of a patch containing the $LTB_4$ agent may also be a useful administration mode.

Additional pharmaceutical methods may be employed to control the duration of action. For example, controlled release preparations may be achieved through the use of macromolecules to complex or absorb the agent. The controlled delivery may be achieved by selecting appropriate macromolecules (for example, polyesters, polyamino acids, polyvinyl pyrrolidone, ethylene-vinyl acetate, methyl cellulose, carboxymethyl cellulose, protamine sulfate or serum albumin, the appropriate concentration of macromolecules, as well as the methods of incorporation. In this manner, release of the agent can be controlled.

Another possible method useful in controlling the duration of action by controlled release preparations is the incorporation of the agent into particles of a polymeric material such as polyesters, polyamino acids, hydrogels, poly(lactic acid), or ethylene-vinyl acetate copolymers.

Instead of incorporating the subject fatty acids into polymeric particles, it is also possible to entrap these materials in microcapsules prepared, for instance, by coacervation techniques or by interfacial polymerization (for example, hydroxymethyl cellulose or gelatin microcapsules and polymethyl methacrylate microcapsules, respectively), in colloidal drug delivery systems (for example, liposomes, albumin microspheres, microemulsions, nanoparticles and nanocapsules) or in macroemulsions. Such techniques are disclosed in Remington's Pharmaceutical Sciences (16th ed. Osol, A., ed., Mack, Easton, Pa. [1980]).

The compositions include compositions suitable for oral or parenteral administration. Conveniently they are presented in unit dosage form and prepared by any of the methods well-known in the art of pharmacy.

In practical use, the $LTB_4$ agent can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions; elixirs and solutions; or carriers such as starches, sugars, microcrystalline cellulose, diluents, granulating agents, lubricants, binders, disintegrating agents and the like in the case of oral solid preparations such as, for example, powders, capsules and tablets. If desired, tablets may be coated by standard aqueous or nonaqueous techniques.

Pharmaceutical compositions of the present invention suitable for oral administration may be presented as discrete units such as capsules, cachets or tablets each containing a predetermined amount of the $LTB_4$ agent, as a powder or granules or as a solution or suspension in an aqueous liquid, a non-aqueous liquid, an oil-in-water emulsion or a water-in-oil emulsion. Such compositions may be prepared by any of the methods of pharmacy such methods including the step of bringing the $LTB_4$ agent into association with the carrier which includes one or more necessary ingredients. In general, the compositions are prepared by uniformly and intimately admixing the $LTB_4$ agent with liquid carriers or finely divided solid carriers or both, and then, if necessary, shaping the product into the desired presentation. For example, a tablet may be prepared by compression of molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

It will be understood that the $LTB_4$ agent is to be administered in pharmacologically or physiologically acceptable amounts, by which is to be understood amounts not harmful to the patient, or amounts where any harmful side effects in individual patients are outweighed by the benefits. Similarly, the $LTB_4$ agent is to administered in a therapeutically effective amount, which is to be understood is an amount meeting the intended therapeutic objectives, and providing the benefits available from administration of $LTB_4$ agent.

The present invention will be more readily understood by referring to the following examples which are given to illustrate the invention rather than to limit its scope.

EXAMPLE I

Assay for EBV-induced Clump Formation and EBNA Synthesis in Peripheral Blood Mononuclear Cells Clump Formation Peripheral blood mononuclear cells (PBMC) were obtained from healthy donors after dextran sedimentation and centrifugation on Ficoll-Paque™ gradients as previously described by Boyum A. (Scand. J. Immunol., 1976, 5(5):9). Cells were resuspended in RPMI-1640 medium supplemented with 10% heat inactivated fetal calf serum (FCS) in the presence of infectious EBV, strain B95-8, at a viral titer of $10^7$ transforming units (TFU)/ml. When indicated, EBV-infected PBMC were simultaneously treated (single addition) with different concentrations of $LTB_4$, i.e. 0.3, 3.0 and 30 nM, respectively. Cells were cultured in 96-well microplates ($10^6$ cells/ml at 200 μl/well) during twelve days, and clump formation, which characterizes the EBV-infected cells was evaluated with an inverted microscope (100 X)(FIG. 1).

Cells were cultured in microplates and the clumps were counted in each well. Results show the mean number of clumps per well+S.D. in one experiment representative of two (2) other. NS: nonstimulated cells.

Detection of Epstein-Barr Nuclear Antigen (EBNA)

Figure 2:
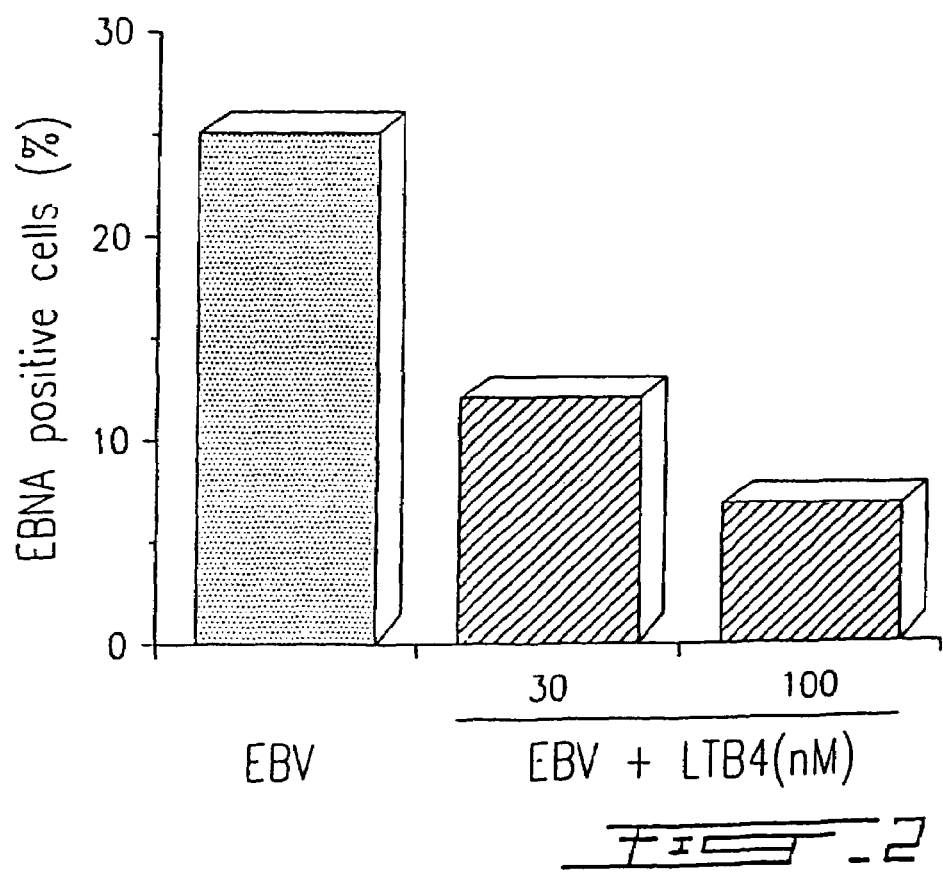
FIG. 2 illustrates the effects of $LTB_4$ on EBV-induced synthesis of Epstein-Barr Nuclear Antigen (EBNA) protein.

In similar experiments, PBMC were infected with EBV and cultured in the presence or absence of $LTB_4$ (Cascade Biochem Ltd., Berkshire, U.K.)($LTB_4$ was added to the concentrations indicated in FIG. 2 at days 0, 3, 6 and 9 of culture). After ten days of culture, cells were harvested for determination of the presence of Epstein-Barr Nuclear Antigen (EBNA), a consequence of EBV infection. Preparation of cell smears, fixation and detection of EBNA by the anti-complement immunofluorescence (ACIF) test were carried out as described by Reedman B. M. and Klein G. (Int. *J. Cancer*, 1973, 11:499). Smears were prepared by spreading 50 µl of a concentrated suspension of washed cells ($2\times10^6$/ml) on clean slides, air dried and fixed in cold acetone ($-20°$ C.) during 10 minutes. Human serum (50 µl) from EBV seropositive donor was used as a source of complement. Slides were incubated at room temperature in a humid chamber during 45 minutes. Slides were then washed three times in phosphate buffer saline (PBS) and stained with 50 µl of fluorescein-5-isothiocyanate (FITC "Isomer I")-conjugated goat IgG fraction anti-human complement C3 (Cappel Research Products, Durham, N.C.) during 60 minutes at room temperature in a humid chamber. Slides were washed in PBS (3 times), mounted in PBS:glycerol 1:1 and examined. Raji and U937 cells were used as positive and negative controls, respectively. The percentage of EBNA-positive cells was decreased by more than 55% with 30 nM $LTB_4$, and by more than 70% with 100 nM $LTB_4$ (FIG. 2). The results illustrated in FIG. 2 are representative of six (6) other experiments. Cells not exposed to EBV showed no detectable EBNA antigen.

Synthesis of EBV Particles

In order to evaluate the effects of LTB4 on the production of newly synthesized viral particles, B95-8 cells, in which EBV replicates, was cultured in the presence or absence of $LTB_4$ (to the concentrations indicated in FIG. 3 at days 0, 5 and 10) during 14 days. The cells were grown in RPMI-1640 medium supplemented with 10% heat inactivated fetal bovine serum (FBS). When the viability of the cells was <20%, cell-free supernatants were harvested and filtered through a 0.45 µm pore size filter, and the viral particles were further concentrated by ultracentrifugation (38,000×g, 160 min., 4° C.). Viral titers were measured by ACIF test on PBMC and expressed in transforming units per ml (TFU/ml). PBMC were then infected with these different EBV preparations and the presence of EBNA was assessed by immunofluorescence (ACIF test). The production of EBV particles was strongly inhibited by 30 nM and 100 nM $LTB_4$, as shown by the decrease of EBNA antigen positive cells (70% and 85%, respectively) (FIG. 3). The results illustrated in FIG. 3 are representative of three (3) other experiments.

EXAMPLE II

Assay for HSV-1 Infection of Peripheral Blood Mononuclear Cells

Detection of Specific HSV-1 Antigen

PBMC were infected with HSV-1 (strain McIntyre) at a $TCID_{50}$ of $10^7$/ml and treated or not with different concentrations of $LTB_4$ ($LTB_4$ was added to the concentrations indicated in FIG. 4 at days 0, 2 and 4) as described in Example I. After five (5) days in culture, the presence of a specific HSV-1 related antigen synthetized in the cytoplasma of infected cells was evaluated by immunofluorescence, using a monoclonal antibody (H62) (ImmunoCorp, Montreal, Canada). Synthesis of the viral antigen was inhibited by 60% in the presence of 100 nM $LTB_4$ (FIG. 4). The results illustrated in FIG. 4 are representative of five (5) other experiments. Similar results (75% inhibition) were obtained by using a specific antiserum (from a chronically infected donor) in immunofluorescence assay.

Synthesis of HSV-1 Particles

In order to evaluate the effect of $LTB_4$ on the synthesis of HSV-1 particles, experiments were performed using Vero cells (obtained from the ATCC). The cells were grown in M-199 medium (Gibco) supplemented with 10% heat-inactivated FBS. When the cells were 80% confluent, supernatants were discarded and adherent cells were infected with HSV-1 ($TCID_{50}$ $10^7$/ml) in M-199 medium supplemented with 2% heat-inactivated FBS, and treated or not with $LTB_4$ ($LTB_4$ was added to the concentrations indicated in FIG. 5 at days 0, 1 and 3). After five days of culture, cell-free supernatants were harvested and filtered through a 0.45 µm pore size filter, and the viral particles were further concentrated by ultra-centrifugation (38,000×g, 160 min, 4° C.). Concentrated viral preparations were suspended in M-199 medium. Freshly cultured Vero cells were then infected with these different HSV-1 preparations and the percentage of infected cells was evaluated by immunofluorescence using a specific antiserum or the H62 monoclonal antibody. The synthesis of HSV-1 particles was strongly inhibited in the presence of 30 nM and 100 nM $LTB_4$ in the cultures as shown by the decrease of HSV-1 antigen positive Vero cells (60% and 70%, respectively) (FIG. 5). The results illustrated in FIG. 5 are representative of four (4) other experiments. Similar results were obtained by infecting PBMC.

Assay for the Antiviral Effect of $LTB_4$ Analogs on EBV and HSV-1 Infections

PBMC were infected with EBV and HSV-1 and treated or not with 100 nM of analogs of LTB4 such as 20-OH-$LTB_4$, $LTA_3$ methyl ester, 12(R)-HETE and 5(S), 15(S)-diHETE. After six days of culture, the presence of EBNA antigen (a consequence of EBV infection) was evaluated by the ACIF test, as described in Example I. Similarly, the presence of HSV-1 antigen in PBMC was evaluated by immunofluorescence using an antiserum obtained from a chronically infected donor as described above in section entitled "Detection of Specific HSV-1 Antigen". The synthesis of EBV or HSV-1 antigen was strongly inhibited in the presence of the $LBT_4$ analogs (100 nM) in the cultures (Table 1). The results illustrated in Table 1 are representative of three other experiments.

TABLE 1

Effect of $LTB_4$ analogs on EBV and HSV-1 infection of PBMC in vitro

| | INFECTION | |
|---|---|---|
| ANALOGS | EBV[1] | HSV-1[1] |
| 20-OH-$LTB_4$ | — | 74% |
| $LTA_3$ methyl ester | 65% | 60% |
| 12(R)-HETE | 65% | 70% |
| 5(S),15(S)-diHETE | 50% | — |

[1]Results are expressed in percentage (%) of inhibition as compared to the infected PBMC cultured in the absence of analogs.

Assay for HSV-1 Infection in vivo

The antiviral effect of $LTB_4$ was also evaluated in an in vivo experimental model-Hairless mice (SKHI strain), from Charles Rivers, 5-6 week old females) were used in these studies. Stock solution of LTB$_4$ (obtained from Cascade Biochem Ltd. Berkshire, U.K.) in ethanol was filtered through a 0.22 μm pore size filter. LTB$_4$ dilutions were prepared at a concentration of 10 μg/100 μl in NaCl 0.9%+glucose 5% (50:50, V/V) containing 0.01% BSA.

For virus inoculation, the mice were immobilized and a small area on the back of the mice was scratched six times with a 27 gauge needle in a crossed-hatched pattern. Forty (40) μl of the virus suspension (HSV-1 strain E-377, $10^7$ TCID$_{50}$/ml) were applied onto the scratched skin area and the virus suspension was rubbed for 20 seconds on the skin using a plastic tip. The infection induced by virus inoculation generated skin lesions, which appeared at the site of inoculation as early as the third day after inoculation and progressed in the form of a 4-5 mm wide band first towards the sides and then towards the abdomen of the mice. Lesions generally were fully developed 5-6 days after inoculation and formed a continuous band extending from the spinal area to the middle of the abdomen. HSV-1-infected mice may also develop symptoms such as posterior limb inflammation, skinniness and showed decreased activity level (lethargy). In this model, animals may die from encephalitis after HSV-1 inoculation.

LTB$_4$ was injected intraperitoneally (100 μl/mice using 1 ml syringe and 23 gauge needle) immediately before virus inoculation (at day 0) and on days 1, 3, 5, 7 and 9 post-inoculation. The mice were housed in groups of five. The groups (5 animals/Group) consisted of 1) non-inoculated mice (a small area on the back of these animals was scratched and rubbed with 40 μl of MEM medium), 2) mice inoculated with HSV-1 receiving intraperitoneal injections of NaCl:glucose+0.01% BSA, and 3) mice inoculated with HSV-1 receiving intraperitoneal injections of LTB$_4$ dissolved in NaCl:glucose+0.01% BSA. Twice a day, mice were observed for measurement of skin lesions, assessment of other symptoms and mortality.

The results obtained indicate that LTB$_4$ exerts a protective effect against HSV-1 infection in vivo. As indicated in Table 2, uninfected animals (Group 1) behaved normally and survived throughout the 14-day period; lesions caused by skin scratching disappeared within 3 or 4 days. HSV-1-infected animals (Group 2) developed lesions (as described above), which were maximal (length) between days 4 to 8; during this same period, mice of this group showed posterior limb inflammation, skinniness and were much less active and almost inert when handled. In HSV-1-infected and LTB$_4$-treated animals (Group 3), lesions also developed from days 0 to 4, but were much smaller (by ~80%) than those observed on animals of Group 2, and regressed from day 8. Furthermore, throughout the experiment, posterior limb inflammation and skinniness were not observed and no deterioration in the general status of the animals was noted, animals remaining active in cages and when manipulated, as for animals of Group 1. All animals survived throughout the experiment; all surviving animals were sacrificed at day 14.

TABLE 2

Effect of LTB$_4$ on herpes simplex type 1 infection in vivo

| GROUP | Size of infected skin lesions (cm)/Infection - associated symptoms[1] | | | | Survival at day 14 |
| --- | --- | --- | --- | --- | --- |
| | Day 4 | Day 6 | Day 8 | Day 10 | |
| Non infected | 0/0 | 0/0 | 0/0 | 0/0 | 100% |
| HSV-1-infected | 1-3/1 | 3-5/2 | 2-5/3 | 1-2/2 | 80% |
| HSV-1-infected + LTB$_4$ treatment | ≦0.5/0 | 1-3/0 | 1-3/0 | ≦0.2/0 | 100% |

[1]Observed symptoms on HSV-1-infected mice:
a) inflammation (swelling) of posterior limbs);
b) skinniness (visual observation);
c) reduced activity (lethargy).
Score:
1: symptom a;
2: symptoms a + b;
3: symptoms a + b + c.

EXAMPLE III

Effect of LTB$_4$ on EBV-induced Tumor Formation in Mice
Assay for EBV Infection in vivo The antiviral effect of LTB$_4$ against EBV was evaluated in an in vivo model using C.B.-17/SCID mice (7-9 week old). Human peripheral blood mononuclear cells (PBL) from healthy donors were obtained by lymphopheresis and purified on Ficoll™ gradients. PBL were then washed in PBS and injected intraperitoneally (i.p.) ($50 \times 10^6$ cells/0.5 ml PBS/mouse) to animals. When indicated, mice were infected i.p. with EBV ($10^6$ TFU). After 30 minutes, mice were treated with LTB$_4$ (i.p.) (10 μg/50 μl NaCl:glucose+0.1% BSA). Additional injections of LTB$_4$ were performed on days 1, 6, 8 (10 μg/mouse), and on days 13, 16, 19, 23, 27, 36 and 40 (5 μg/mouse) post-infection. Four groups of SCID mice were constituted as follows:

Group 1: treated with NaCl:glucose+0.1% BSA (5 mice) (placebo)

Group 2: treated with LTB$_4$ (5 mice)

Group 3: EBV-infected and treated with NaCl:glucose+0.1% BSA (10 mice)

Group 4: EBV-infected and treated with LTB$_4$ (10 mice).

EBV is known as an oncovirus which causes the growth of tumor cells in vivo. The effect of LTB$_4$ on tumor formation was then evaluated. Mice were kept in a sterile room and observed three times a week until the apparition of tumors and then twice a day to monitor the growth of tumors. On day 42, mice were bled and sacrificed (cervical dislocation). Post-mortem analysis was performed on all animals. Mice were autopsied, photos were taken and spleen and tumors were measured and snap-frozen in dry ice/EtOH for later molecular analysis.

The results obtained indicate that LTB$_4$ reduces tumor growth induced by EBV. Uninfected mice treated with NaCl solution or with LTB$_4$ alone behaved normally and survived throughout the 42-day period. Five (out of nine) EBV-infected animals develop tumors larger than 800 mm$^3$, and two had tumors >1,500 mm³ (Table 3). In animals infected with EBV and treated with LTB$_4$, only three mice had tumors larger than 800 mm³, none developed tumors larger than 1,500 mm³ and tumors were smaller than 800 mm³ in six (out of nine) animals. The enlargement of the spleen was somewhat more pronounced in EBV-infected than in LTB$_4$-treated EBV-infected animals.

TABLE 3

Effect of LTB$_4$ on EBV-induced splenomegaly and tumor growth

| GROUPS[1] | SPLENOMEGALY | | | TUMOR SIZE (mm³) | | |
|---|---|---|---|---|---|---|
| | Normal | Enlarged | Very enlarged | <800 | 800-1500 | >1500 |
| EBV-infected[2] | 0/9 | 5/9 | 4/9 | 2/9 | 5/9 | 2/9 |
| EBV-infected[3] + LTB$_4$ treatment | 1/9 | 6/9 | 2/9 | 6/9 | 3/9 | 0/9 |

[1]Results are expressed as the number of mice affected over the number of mice in each group. Two EBV-infected mice treated with LTB4 died at days 41 and 42, and one EBV-infected mouse died at day 42. These mice were autopsied and the results were included in Table 1. Uninfected mice injected with NaCl: glucose + 0.1% BSA, or with LTB4 were normal. All animals were sacrificed on day 42.
[2]One mouse of this group died at day 37 post infection. The autopsy revealed the presence of large tumors (>1500 mm3). Hemorrhage was observed. Spleen was enlarged.
[3]One mouse of this group died at day 32 post infection. The autopsy revealed no abnormality nor the presence of tumors.

EXAMPLE IV

Assay for HIV-1-Infection of Peripheral Blood Mononuclear Cells

The antiviral properties of LTB$_4$ on HIV-1-infection were also evaluated.

Reverse Transcriptase Activity in HIV-1-infected Cells

PBMC were resuspended at a density of 10⁶ cells/ml in culture medium (RPMI-1640 supplemented with 10% FBS), and cultured in the presence of 3 µg/ml PHA-P (Sigma, St.Louis, Mo.) and 30 U/ml of recombinant human IL-2 for 2 to 3 days at 37° C. under a 5% CO$_2$ atmosphere. PHA-stimulated PBMC were resuspended at 1×10⁶ cells/ml and were infected with HIV-1$_{IIIB}$ (various multiplicity of infection: number of infectious virus particles/target cell) in the absence or the presence of increasing concentrations of LTB$_4$ (0, 30, 100, and 200 nM). The culture media were changed twice a week and appropriate amounts of LTB$_4$ were added at every medium change. Cell-free culture supernatants were frozen at specific time periods until assayed. Virus replication was monitored either by reverse transcriptase or p24 assays.

Virus stocks were prepared from acutely infected cells. In brief, Molt 4 clone 8 were infected with HIV-1$_{IIIB}$ At the maximal virus production and before extensive cytopathic effects were seen, cells were centrifuged at 300×g for 5 minutes and the virus-containing supernatant was clarified at 2000×g for 30 minutes and was filtered through a 0.45 µm cellulose acetate membrane to remove cellular debris. Thereafter, the virus-containing supernatants were stored at −80° C. in aliquots. Titration of infectivity was performed by terminal dilution micro assay using the highly susceptible MT-4 cell line.

Reverse Transcriptase Assay

Enzymatic activity was measured with 50 µl of cell-free supernatant to which 10 µl of a solution A (5 mM dithiothreitol, 50 mM KCl, 0.05% Triton X-100) and 40 µl of a solution B (5 mM MgCl$_2$, 0.5 M EGTA, 0.04 mg of poly(rA)-oligo (dT)$_{12-18}$, 3 mCi [³H]TTP (40 to 70 Ci/mmol) had been added. After incubation for 1 hour at 37° C., samples were precipitated with one volume of a solution containing 0.15% pyrophosphate and 1.66% trichloroacetic acid prior filtration onto glass fiber filters by using a cell harvester system. The filters were dried and radioactivity was measured in a liquid scintillation counter (1205/1204 BS Beta-plate; Wallac Oy, Turku, Finland). The assays were performed in triplicate.

Enzymatic p24 Assay

Quantitative determination of the main viral core p24 protein was achieved with the use of a commercial enzyme-linked immunosorbent assay (Organon Teknika, Durham, N.C.).

Figure 6A:
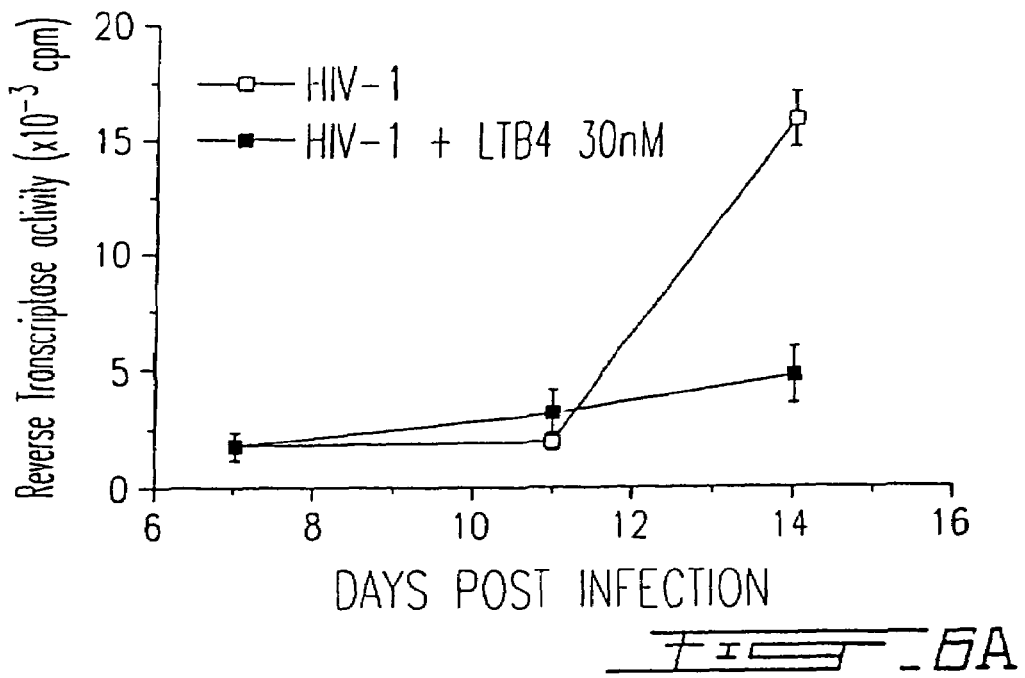
FIGS. 6A and 6B illustrate the effects of $LTB_4$ on reverse transcriptase activity in HIV-1 infected peripheral blood mononuclear cells.
Figure 6B:
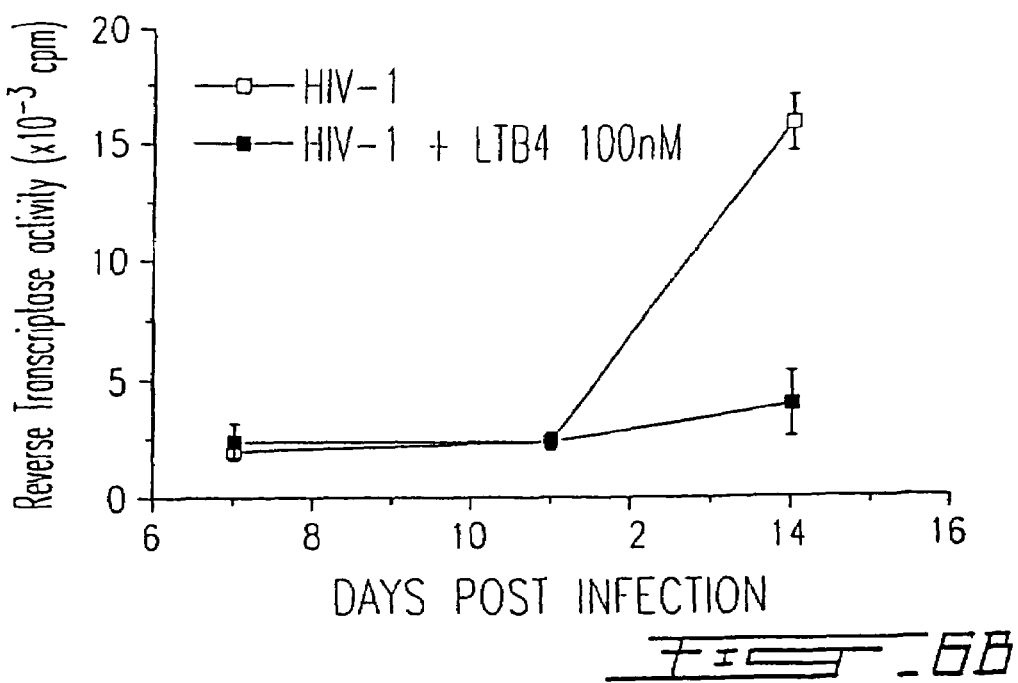

When LTB$_4$ was present in the culture media, the viral activity of HIV-1 in PBMC evaluated after two weeks of culture was reduced by more than 70% (see FIGS. 6A and 6B). The results illustrated in FIGS. 6A and 6B are representative of three (3) other experiments. Similar results were obtained by monitoring the p24 release in supernatants.

Synthesis of HIV-1 Particles

This set of experiments was carried out with the J1.1 cell line, a latently injected cell line derived from the parental cell line Jurkat E6.1. J1.1 cells were resuspended at a density of 10⁶ cells/ml in culture medium (RPMI-1640 supplemented with 10% FBS) and were stimulated with the phorbol ester PM-A (20 ng/ml) in the absence or the presence of increasing concentrations of LTB$_4$ (0,30, 100 nM). LTB$_4$ was again added (to the same concentrations) 24 hours after the initiation of the cultures. After 48 hours of culture, cell-free supernatants were harvested and the presence of infectious HIV-1 particles was quantitated by end-point titration assay.

End-point Titration Assay (TCID$_{50}$)

End-point titration was carried out in flat-bottom microtiter wells using four parallel series of ten-fold dilutions of cell-free supernatants. After 5 to 7 days of incubation with MT-4 cells, cell-free supernatants were harvested and tested for the major viral core p24 protein by a commercially available enzymatic assay. The TCID$_{50}$ was calculated by the method of Reed and Muench.

Our results clearly demonstrate that 100 nM LTB$_4$ inhibited the synthesis of HIV-1 particles in J1.1 cells by 55% to 79% (Table 4).

TABLE 4

Inhibition of HIV-1 particles synthesis in J1.1 cells by LTB$_4$

| Experiment | Non treated | LTB$_4$-treated 30 nM | LTB$_4$-treated 100 nM |
|---|---|---|---|
| 1 | 1000[1] | 511 (49%) | 447 (55%) |
| 2 | 1143 | 575 (50%) | 448 (61%) |
| 3 | 4630 | 2053 (56%) | 981 (79%) |

J1.1 cells were treated or not with LTB$_4$.
[1]Number of viral particles evaluated by end-point titration assay (TCID$_{50}$) as described in Example IV.
Numbers in parenthesis indicate the percentage of inhibition induced by LTB$_4$.

EXAMPLE V

Assay for HIV Infection in vivo

Forty 6-10 week old C.B-17 SCID mice were reconstituted with $40 \times 10^6$ peripheral blood mononuclear cells (PBMC) obtained from healthy volunteer. Two hours after reconstitution, 30 mice were infected with 50 $TCID_{50}$ of non-syncytium-inducing primary isolate of HIV (93US151) by intraperitoneal injection (I.P.). Mice were divided into 4 groups:

Group 1: Uninfected placebo control,

Group 2: HIV-infected and treated with placebo,

Group 3: HIV infected and treated intraperitoneally with 1 ng/mouse of $LTB_4$ once a day from day 1 to day 14, Group 4: HIV-infected and treated intraperitoneally with 10 ng/mouse of $LTB_4$ once a day from day 1 to day 14, Group 5: HIV infected and treated intraperitoneally with 100 ng/mouse of $LTB_4$ once a day from day 1 to day 14.

On day 7 post-infection (P.I.), blood samples were drawn from each mice from the retro-orbital venous plexus and anticoagulated with 50 mM EDTA. Plasma were separated by centrifugation and stored at $-70°$ C. Blood samples were also drawn on day 14 P.I., as described above. In addition, on day 14 P.I., engrafted human cells were harvested by washing the peritoneal cavity with 7 ml of RPMI culture medium. The percentage of CD4+ T cells in the peritoneal caviy of each mice was determined by flow cytometry using FITC-labelled anti-human HLA class I antibody and PE-labeled anti-human CD4 antibody. The number of CD8+ T cells was also evaluated by flow cytometry. Mean±S.D. of percentage of CD4+ T cells in control and experimental groups were compared and evaluated. In addition, the HIV plasma viral load from each mice was evaluated at days 7 and 14 P.I. by competitive PCR assays (Amplicor HIV-1 Monitor; Roche Molecular Systems). As shown in FIG. 7A, the percentage of CD4+ T cell survival was significantly increased in HIV-1 infected mice treated with $LTB_4$ as compared to those treated with placebo. HIV viral loads were also reduced in animals treated with $LTB_4$ when compared to the placebo-treated group (FIG. 7B).

EXAMPLE VI

Assay for $LTB_4$ Cytotoxicity

Figure 8:
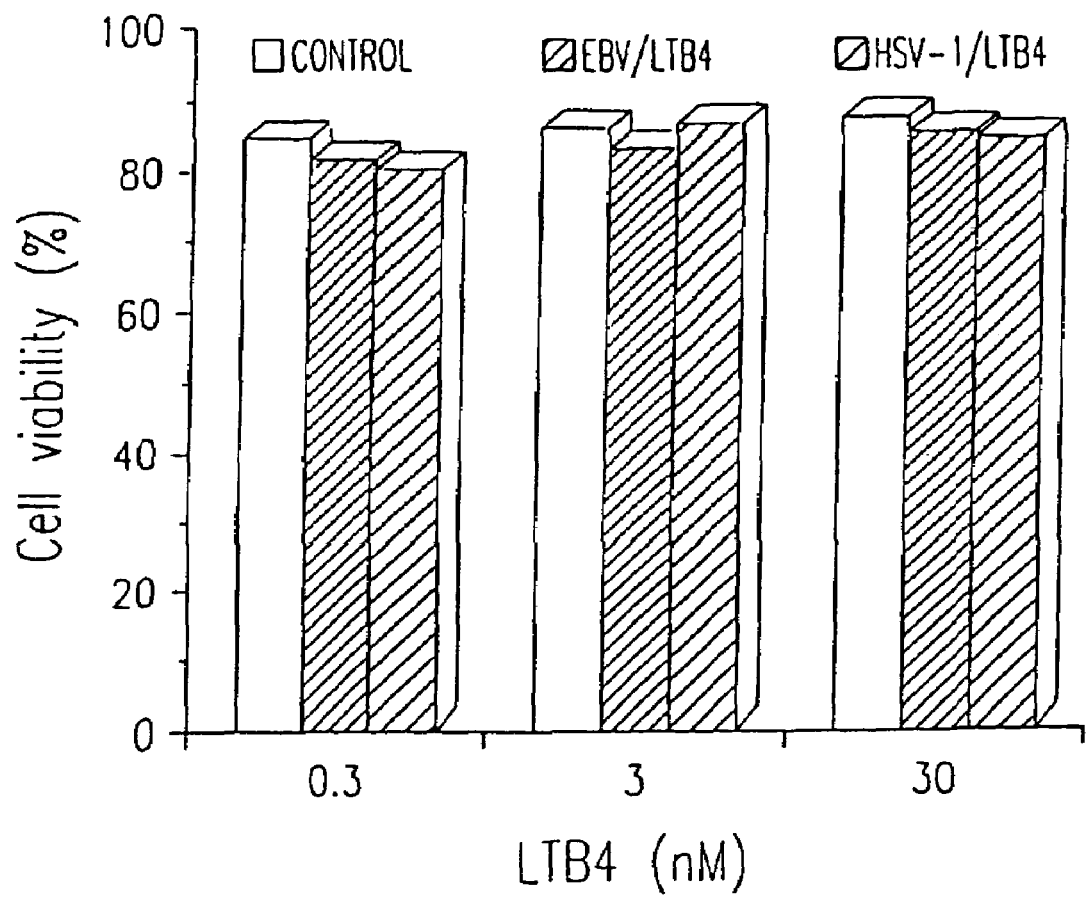
FIG. 8 illustrates the effects of $LTB_4$ on cell viability.

In cell cultures described in Examples I and II, the cytotoxic effect of $LTB_4$ was assessed by the trypan blue dye exclusion test at concentrations up to 30 nM. $LTB_4$ was found to exert no cytotoxic effect (FIG. 8). Cell viability was assessed by the trypan blue exclusion test; values (from 1 experiment representative of 3) represent the mean cell viability in cell cultures (n=24).

EXAMPLE VII

Antiviral Effects of $LTB_4$ and Acyclovir on EBV Infection

Figure 9A:
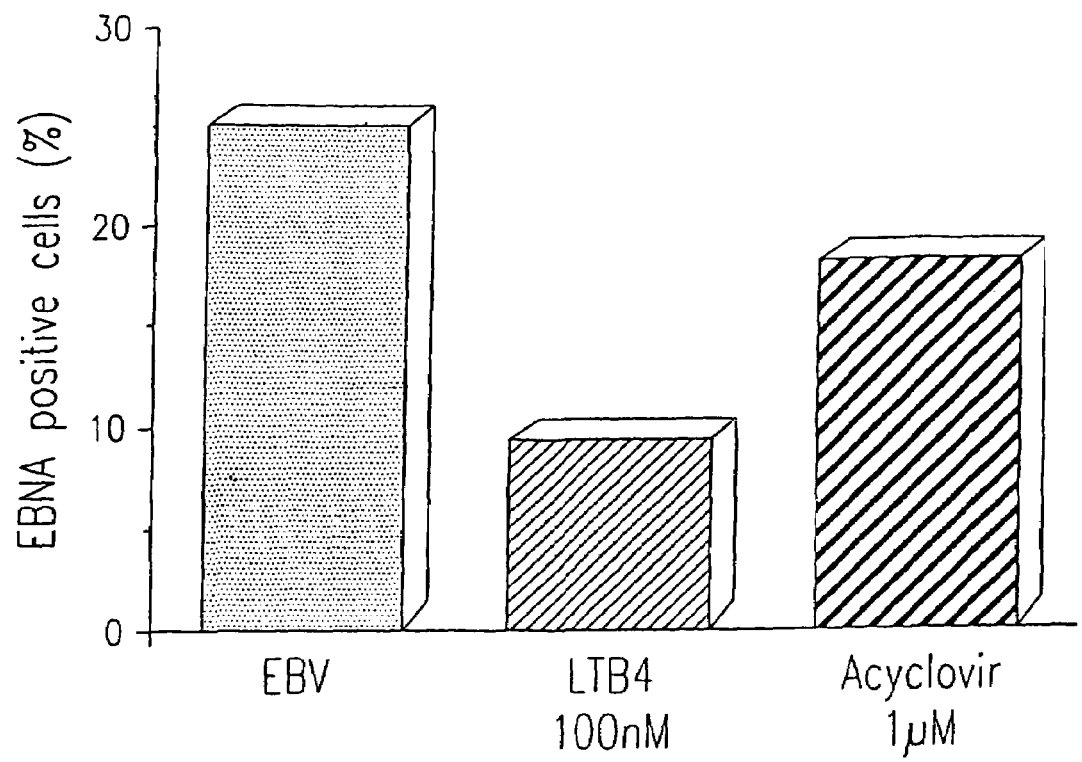
FIGS. 9A and 9B illustrate the effects of $LTB_4$ and acyclovir on EBV-induced synthesis of EBNA protein (A), and also on HSV-1-induced synthesis ofc viral proteins (B)
Figure 9B:
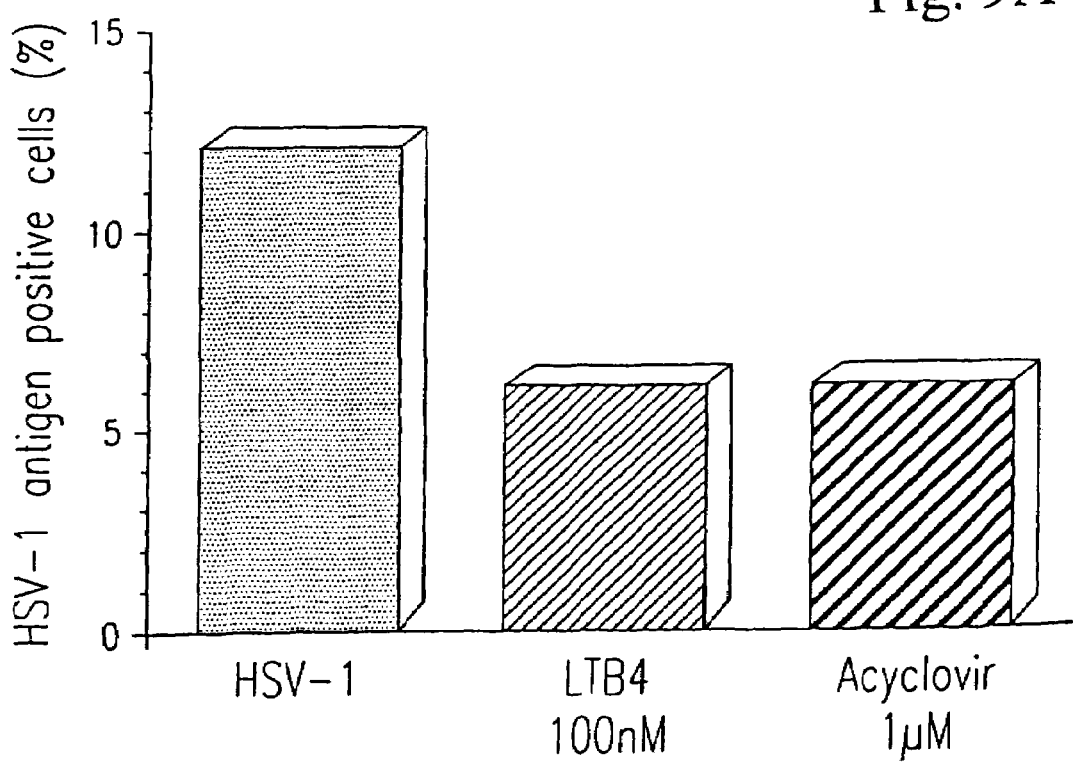

PBMC ($10^6$ cells/ml) were cultured in microplates (96 wells) at $2 \times 10^5$ cells/well and infected with EBV ($10^7$ TFU/ml) or HSV-1 ($10^7$ $TCID_{50}$/ml) as described in Examples I and II, respectively. At one hour post-infection, cell cultures were treated with $LTB_4$ (100 nM) or with acyclovir (acycloguanosine)(1000 nM). Drugs were added every 48 hours of culture. EBV and HSV-1 infections were evaluated at days 7 and 6, respectively, by evaluating the synthesis of viral antigens (FIGS. 9A and 9B) as described in Examples I and II. The results illustrated in FIGS. 9A and 9B are from 1 experiment, representative of four (4) others. acyclovir was tested at 1 µM only.

Detection of viral antigens were performed by immunofluorescence on 36 cultures.

EXAMPLE VIII

Effect of $LTB_4$ on the Biological Activity of Acyclovir

Figure 10:
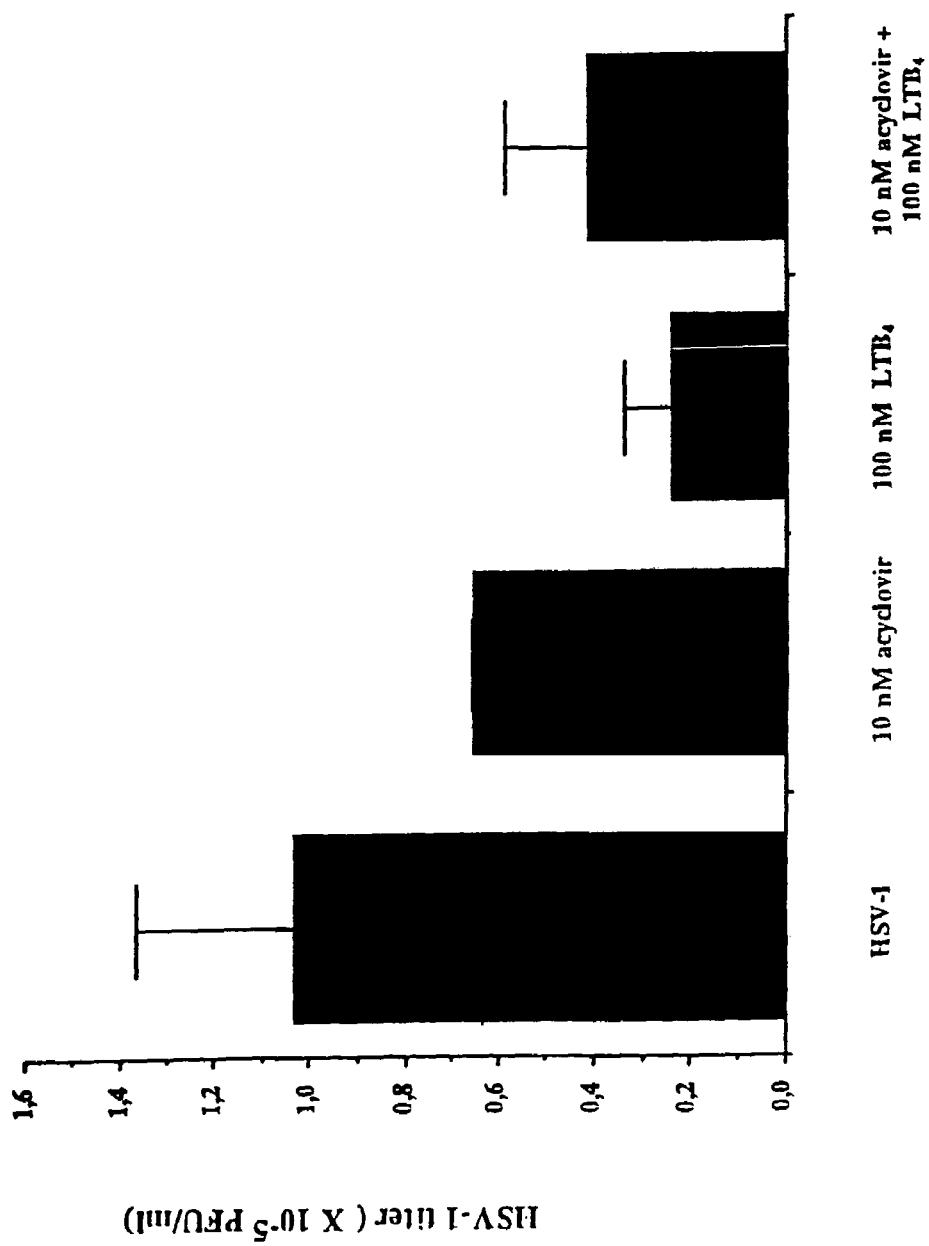
FIG. 10 illustrates the effect of acyclovir, $LTB_4$ or both on HSV-1 infected cells.

PBMC ($10^6$ cells/ml) were infected with HSV-1 and treated with acyclovir or with $LTB_4$ or with a combination of both drugs. A suboptimal concentration of acyclovir was used to assess the effect of $LTB_4$ on the biological activity of acyclovir. After four days of culture, cell-free supernatants containing viral particles were harvested and the number of particles was titrated by plaque assay on Vero cell monolayers. Briefly, 0.2 ml of serially diluted ($log_{10}$) culture supernatants to be tested were added to confluent monolayers of Vero cells in duplicate for 1 hour at $37°$ C. Unadsorbed particles were removed by washing and minimal media containing 1% methyl cellulose was added to the monolayers. Between days 5 to 7 post-infection, the cultures were fixed with methanol and stained with crystal violet. The number of plaques (PFU: plaque forming units), reflective of the number of infectious particles, were counted and the viral titer from each experimental group determined, and the effective inhibitory dose calculated. The results obtained show that $LTB_4$ does not reduce the antiviral effect of acyclovir in co-culture conditions (FIG. 10). The results illustrated in FIG. 10 are representative of five others.

EXAMPLE IX

Effect of $LTB_4$ in an HIV ex vivo Model

It is well known that critical events in the progression of AIDS occur in lymphoid tissue. In vitro studies using isolated cells cannot mimic the full cellular repertoire found in lymphoid tissue, nor their fully immunological functions. In addition, animal models neither possess the characteristic tissue pathology of human HIV infection.

An ex vivo model that retains the cellular organization found in normal human lymphoid tissue was used. The selected lymphoid tissues were tonsils. Immunohistochemical analyses revealed that tonsils are formed of B and T cells, macrophages and follicular dendritic cells. Such an ex vivo model is used to study HIV pathogenesis and potency of antiviral agents such as AZT (Zidovudine) by many laboratories.

Human tonsillar tissues from two different individuals were removed during routine tonsillectomy and were received within five hours of excision. The tonsils were washed thoroughly with medium supplemented with antibiotics and then sectioned into 2-3 mm blocks. These tissue blocks were placed in culture medium at the air-liquid interface on the top surface of collagen sponge gels and were pretreated for 10 min with the indicated concentrations of LTB4 (0.01, 0.1 and 1 µM). Next, HIV-1 particles (400 TCID50 of HIV-1 strain 89.6) were applied at the top of each tissue block. The next day, the culture medium was completely removed and replaced with fresh medium supplemented with a final concentration of LTB4 (0.01, 0.1 and 1 µM). This step is necessary in order to remove unadsorbed and uninternalized virus particles. Productive HIV-1 infection was assessed every 3 to 4 days by measuring p24 in the culture medium using a viral core p24 antigen enzyme-linked immunosorbent assay. The medium was also changed every 3 to 4 days and was replaced with fresh culture medium containing a final concentration of LTB4 (0.01, 0.1 and 1 µM).

Results

Figure 11:
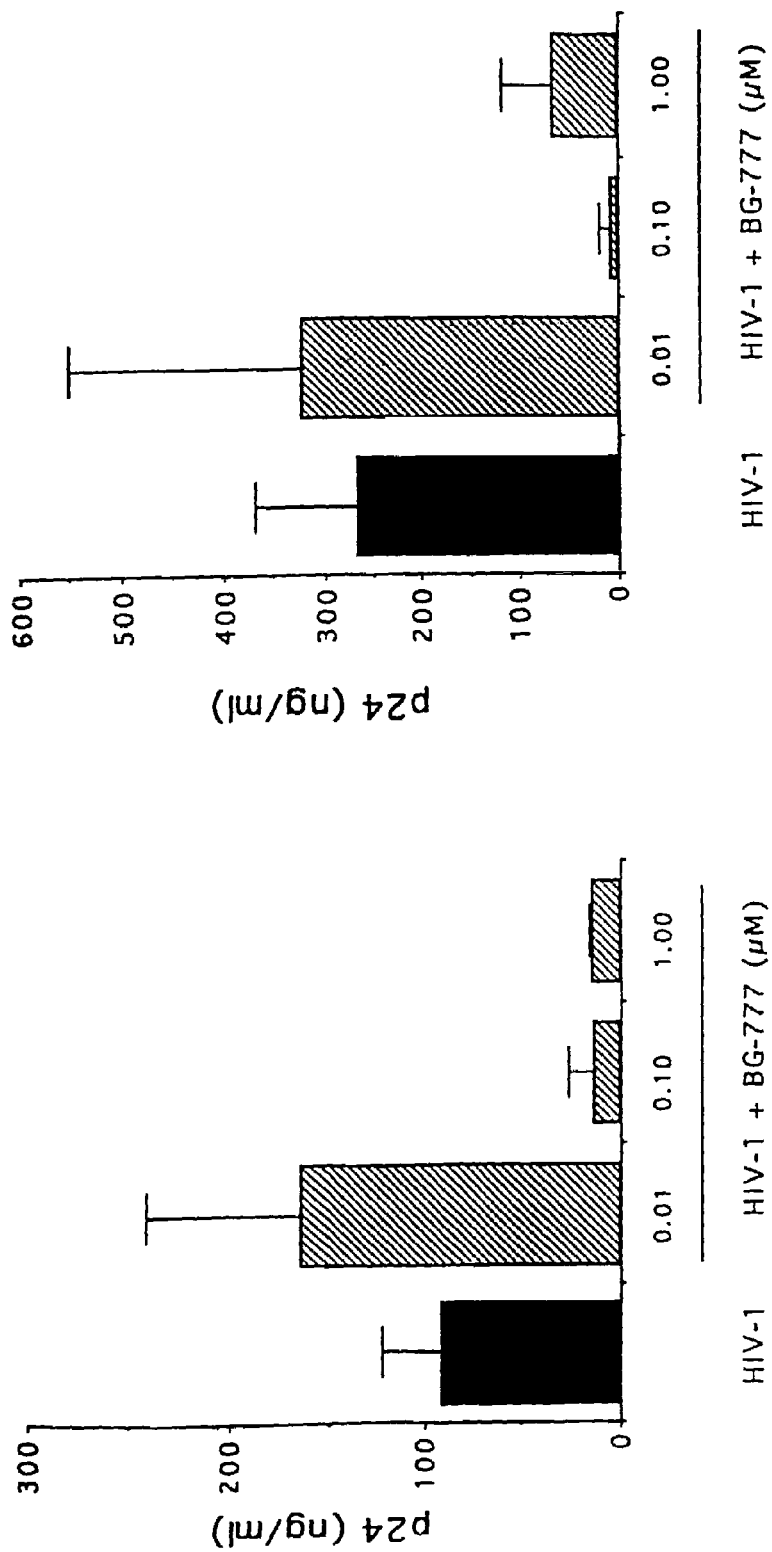
FIG. 11 illustrates the effect of $LTB_4$ on the release of p24 in an HIV-1 ex vivo model.

As shown on FIG. 11, LTB4 strongly inhibited the replicative cycle of HIV-1 by more than 75%. Results from LTB4-treated tonsils are significantly different (p<0.05) from those from tonsils treated with placebo.

EXAMPLE X

Assays for the Efficacy of $LTB_4$ on the CMV Viral Load

Several parameters can be monitored to determine the efficacy of antiviral agents. The Applicants have chosen to monitor very objective parameters such as body temperature, weight loss/gain, mortality and the CMV viral load in several organs of infected mice. Results showing the efficacy of $LTB_4$ on body temperature, weight loss/gain and mortality of CMV infected mice are discussed above. The Applicants now extend and reconfirm the results on the efficacy of $LTB_4$ by measuring a reduction in the CMV viral load in lungs and salivary glands of infected mice.

Six week old BALB/c mice were infected by intravenous injection with $10^4$ plaque forming units (PFU) of murine CMV (Smith strain). Mice were divided into two groups: the first group received a placebo while the second group was treated with 25 ng of $LTB_4$, administered intravenously once a day starting on the day of infection. After 12 days of treatment, mice were sacrificed and the lungs and salivary glands harvested. The organs were homogenized, in 0.5 ml of culture medium, to liberate intracellular viral particles. After centrifugation, the cell free supernatants were tested for the presence of CMV particles by standard plaque assay technique. Briefly, serially diluted supernatants were added to a monolayer of mouse embryonic fibroblast cells (highly susceptible to CMV infection) for 1 hour at 37° C. after which the nonadsorbed virus were removed and the monolayer overlaid with 1.5% methylcellulose. After a 5-day incubation, the monolayers were fixed with formaldehyde and stained with violet crystal. The number of plaques, which represents areas of infection equivalent to one viral particle, were counted and the CMV titers in the lungs and salivary glands determined.

Figure 12A:
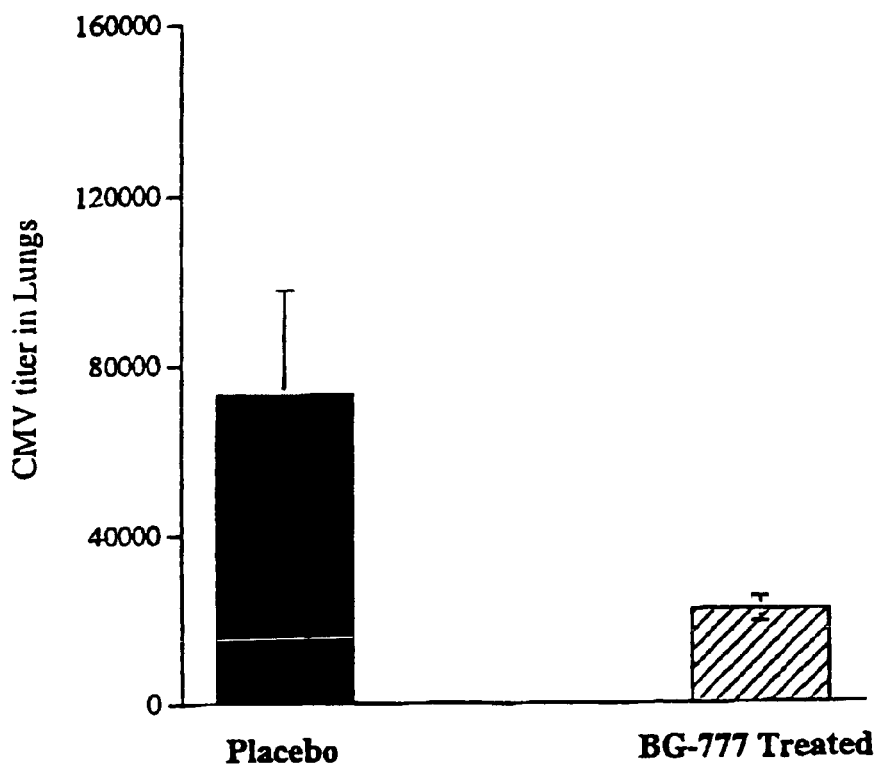
FIG. 12A illustrates the effect of $LTB_4$ on viral load of CMV-infected mice in lungs.

As shown in FIG. 12A, a 77% reduction ($p \leq 0.005$) in the CMV viral load in the lungs of $LTB_4$-treated mice was observed compared to the CMV viral load in the lungs of placebo-treated mice. Also, as shown in FIG. 12B, a 70% glands of $LTB_4$-treated mice was observed compared to the CMV viral load in the salivary glands of placebo treated mice.

EXAMPLE XI

Effect of $LTB_4$ Administration on Human Coronavirus Infection in Lungs of Mice The antiviral effect of $LTB_4$ in controlling pneumonia caused by coronavirus was evaluated in an in vivo model using C57BL/6 mice (8 day old). Mice were infected (n=6/group) intranasally with 10 μl of coronavirus suspension ($10^4$ PFU, strain HCoV-OC43). Twenty-four hours post-infection, mice were treated intranasally with a placebo or with varying doses of $LTB_4$ (5 ng/dose or 50 ng/dose). Mice were treated once a day during 5 days, and were sacrificed and autopsied on day 6. Lungs of mice were surgically removed and the viral load was titrated on HRT-18 cell line. The results obtained indicate that LTB4 significantly reduces the number of coronavirus particles in lungs of mice (Table 5).

TABLE 5

Effects of intranasal administration of $LTB_4$ on human coronavirus infection in lungs of mice

| Mice | $LTB_4$ (5 ng/dose/mouse) | $LTB_4$ (50 ng/dose/mouse) | Placebo |
|---|---|---|---|
| #1 | N.D. | N.D. | N.D. |
| #2 | N.D. | N.D. | N.D. |
| #3 | N.D. | N.D. | 100 * |
| #4 | N.D. | N.D. | 56 |
| #5 | N.D. | N.D. | 316 |
| #6 | N.D. | N.D. | 562 |

* PFU/lungs
N.D. = below detection limit of 32 $TCID_{50}$/lungs

EXAMPLE XII

Effect of $LTB_4$ on Influenza Infection in Lungs of Mice

Figure 13:
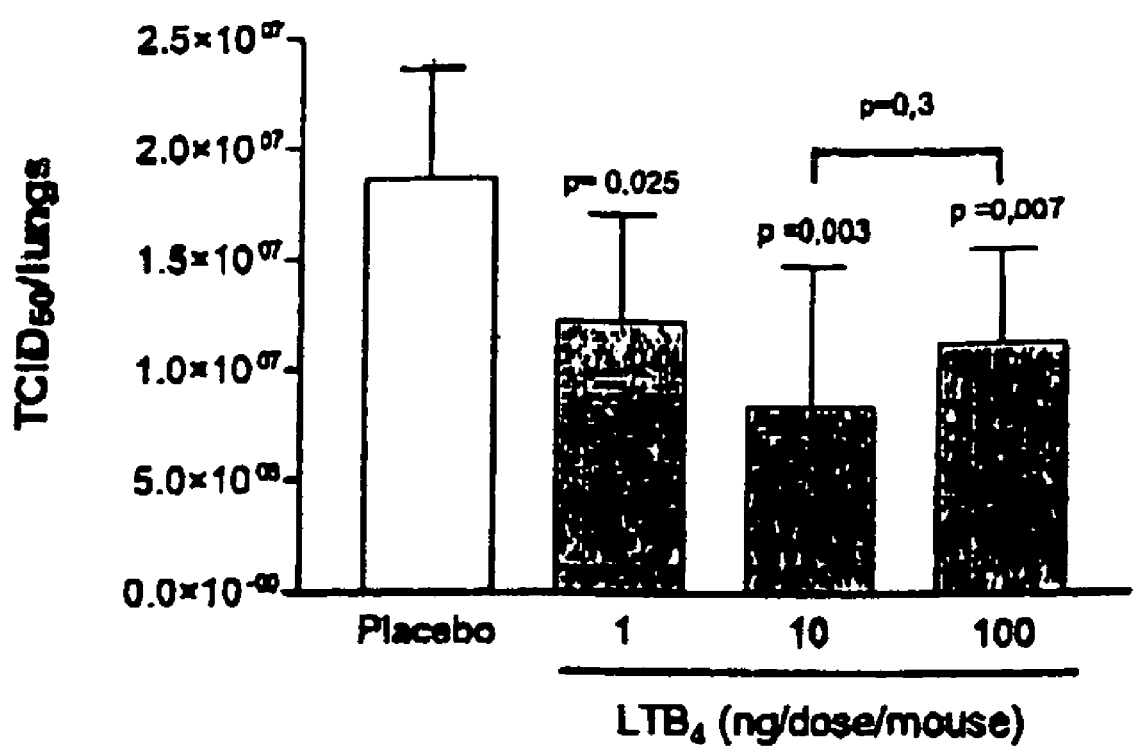
FIG. 13 illustrates the effect of LTB4 on viral load of Influenza virus-infected mice in lungs.

The efficacy of $LTB_4$ to reduce influenza infection in lungs of mice was also demonstrated. BALB/c mice (6-8 week old) were infected (n=6/group) by delivering 10 PFU of influenza virus (strain A/Pr/8/34) in the nasal cavity. On days 1 to 5 post-infection, mice were treated intranasally with a placebo or with varying doses of $LTB_4$ (1, 10 and 100 ng/dose). On the 6th day post-infection, all mice were sacrificed and influenza viral loads in lungs were determined using the MDCK cell line. The results (FIG. 13) show that influenza titers in the lungs were significantly decreased in mice that have received $LTB_4$ locally in the airways.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the treatment of an enveloped RNA viral infection in a human or animal comprising administering to a human or animal in need of such treatment, a pharmacologically acceptable therapeutically effective amount of exogenous $LTB_4$ agent selected from the group consisting of 5,12-dihydroxy-6,8,10,14-eicosatetraenoic acid, 5-hydroxy-6,8,11,14-eicosatetraenoic acid, 20,20,20-trifluoromethyl-$LTB_4$; 19-methyl-$LTB_4$, 19,19-dimethyl-$LTB_4$, 19-fluoro-$LTB_4$, 19,19-difluoro-$LTB_4$, 18,20-difluro-$LTB_4$, 20-fluoro-$LTB_4$, 3-thio-$LTB_4$, 3-hydroxy-$LTB_4$, 3-methyl-$LTB_4$, 3,3-dimethyl-$LTB_4$, 3-fluoro-$LTB_4$, 3,3-difluoro-$LTB_4$, 2,3-difluoro-$LTB_4$; 14,15-dihydro-$LTB_4$("$LTB_3$"), 17,18-dehydro-$LTB_4$ ("$LTB_5$"), 19-hydroxy-$LTB_4$, 20-hydroxy-$LTB_4$ and 5(R)-hydroxy, 5-keto, 5(S)hydroperoxy, 5(R)-hydroperoxy and 5-deoxy analogs thereof; $LTB_4$ methyl ester; 5,12-dihydroxy-6,8,10,14-eicosatetraenoic acid; 20,20,20-trifluoromethyl-$LTB_4$; and 5S,12R-dihydroxy-6,8,10,14(Z,E,E,Z)-eicosatetraenoic acid and any salts and mixtures thereof.

2. A method according to claim 1, wherein said $LTB_4$ agent is a salt thereof.

3. A method according to claim 1, wherein said viral infection is selected from the group consisting of togaviridae, orthomyxoviridae, paramyxoviridae, coronaviridae, filoviridae.

4. A method according to claim 3, wherein said viral infection is orthomyxoviridae.

5. A method according to claim 1, wherein said agent is leukotriene $B_4$ [5S,12R-dihydroxy-6,8,10,14(Z,E,E,Z)-eicosatetraenoic acid].

6. A method according to claim 1, wherein said $LTB_4$ agent is selected from the group consisting of 14,15-dihydro-$LTB_4$ ("$LTB_3$"), 17,18-dehydro-$LTB_4$("$LTB_5$"), 19-hydroxy-$LTB_4$, 20-hydroxy-$LTB_4$ and 5(R)-hydroxy, 5-keto, 5(S)hydroperoxy, 5(R)-hydroperoxy and 5-deoxy and salts thereof.

7. A method according to claim 1, wherein said $LTB_4$ agent is 5,12-dihydroxy-6,8,10,14-eicosatetraenoic acid.

8. A method according to claim 1, wherein said $LTB_4$ agent is selected from the group consisting of 20,20,20-trifluoromethyl-$LTB_4$; 19-methyl-$LTB_4$, 19,19-dimethyl-$LTB_4$, 19-fluoro-$LTB_4$, 19,19-difluoro-$LTB_4$, 18,20-difluro-$LTB_4$, 20-fluoro-$LTB_4$.

9. A method according to claim 1, wherein said $LTB_4$ agent is selected from the group consisting of 3-thio-$LTB_4$, 3-methyl-$LTB_4$, 3,3-dimethyl-$LTB_4$, 3-fluoro-$LTB_4$, 3,3-difluoro-$LTB_4$, 2,3-difluoro-$LTB_4$.

10. A method according to claim 1, wherein said $LTB_4$ agent is a sodium salt thereof.

11. A method according to claim 1, wherein said $LTB_4$ agent is a potassium salt thereof.

12. The method of claim 1, wherein said administration is effected orally, intraarterially, intravenously, intraperitoneally, subcutaneously, intramuscularly, sublingually, intranasally, parenterally, topically, by inhalation or by suppository.

13. The method of claim 4, wherein said orthomyxoviridae is influenza virus.

* * * * *